US010966996B2

(12) United States Patent
Zhu et al.

(10) Patent No.: US 10,966,996 B2
(45) Date of Patent: Apr. 6, 2021

(54) *GLECHOMA LONGITUBE* EXTRACT, PREPARATION METHOD FOR SAME, AND USE THEREOF IN SUGAR REDUCTION, WEIGHT LOSS, AND LIPID REDUCTION

(71) Applicants: SHANGHAI INSTITUTE OF MATERIA MEDICA CHINESE ACADEMY OF SCIENCES, Shanghai (CN); NANJING PAILEXING PHARMACEUTICAL TECHNOLOGY LTD., Jiangsu (CN)

(72) Inventors: Weiliang Zhu, Shanghai (CN); Heyao Wang, Shanghai (CN); Yong Zhang, Shanghai (CN); Peng Sun, Shanghai (CN); Bo Li, Shanghai (CN); Zhijian Xu, Shanghai (CN); Hualiang Jiang, Shanghai (CN); Kaixian Chen, Shanghai (CN)

(73) Assignees: SHANGHAI INSTITUTE OF MATERIA MEDICA CHINESE ACADEMY OF SCIENCES, Shanghai (CN); NANJING PAILEXING PHARMACEUTICAL TECHNOLOGY LTD., Nanjing (CN)

( * ) Notice: Subject to any disclaimer, the term of this patent is extended or adjusted under 35 U.S.C. 154(b) by 309 days.

(21) Appl. No.: 15/126,676

(22) PCT Filed: Mar. 17, 2015

(86) PCT No.: PCT/CN2015/074366
§ 371 (c)(1),
(2) Date: Sep. 16, 2016

(87) PCT Pub. No.: WO2015/139603
PCT Pub. Date: Sep. 24, 2015

(65) Prior Publication Data
US 2017/0087173 A1  Mar. 30, 2017

(30) Foreign Application Priority Data

Mar. 17, 2014 (CN) .......................... 2014 1 0104913

(51) Int. Cl.
*A61K 36/00* (2006.01)
*A61K 31/7048* (2006.01)
*A61K 36/53* (2006.01)

(52) U.S. Cl.
CPC .......... *A61K 31/7048* (2013.01); *A61K 36/53* (2013.01); *A61K 2236/30* (2013.01); *A61K 2236/53* (2013.01)

(58) Field of Classification Search
None
See application file for complete search history.

(56) References Cited

FOREIGN PATENT DOCUMENTS

| CN | 103113196 A | 5/2013 |
|---|---|---|
| CN | 103340991 A | 10/2013 |
| JP | 9-143070 A | 6/1997 |
| JP | 2007-99635 A | 4/2007 |
| JP | 2008-509988 A | 4/2008 |
| JP | 2008-199973 A | 9/2008 |
| JP | 2012-171951 A | 9/2012 |
| KR | 100793019 B1 | 1/2008 |
| KR | 10-0905437 B1 | 7/2009 |
| KR | 10-2013-0089385 A | 8/2013 |
| WO | 2006/018743 A2 | 2/2006 |

OTHER PUBLICATIONS

European Search Report dated Feb. 20, 2017 for the corresponding European Application No. 15765481.5.
Yang, Nian-Yun et al., "Chemical Constituents of Glechoma Longituba," Chinese Journal of Natural Medicines, Zhongguo Tianran Yaowu, Nanjing, CN, vol. 4, No. 2, Mar. 31, 2006, pp. 98-100.
Ni, Shu-mao et al., "Qualitative and quantitative analysis of the major bioactive phenolic compounds of Glechoma longituba by LC-coupled with PAD and ESI-MS detection," Natural Products Communications, vol. 6, No. 1, Jan. 1, 2011, pp. 17-20.
S.P. Dhanabal et al., "Antidiabetic Activity of Clerodendron phiomoidis Leaf Extract in Alloxan-Induced Diabetic Rats," Indian Journal of Pharmaceutical Sciences, Nov. 1, 2008, pp. 841-844.
Berashvili et al., Luteolin diglucuronide from Perilla nankinensis. Chemistry of Natural Compounds. Jan. 2006;42(1):106-107.
Carnat et al., Luteolin 7-diglucuronide, the major flavonoid compound from Aloysia triphylla and Verbena officinalis. Planta Med. Oct. 1995;61(5):490, 3 pages.
Chen et al., Spectral analysis of clerodendrin, isolated from Clerodendron trichotomum Thunb. Yao Xue Xue Bao. 1988;23(10):789-91.
Ping et al., Pharmacy (Scholars) Qualification Examination Guide [M]. Beijing: Military Medical Science Publishing House. 2012;1:57-61.
Xiaoying et al., Study on Separation and Purification of Total Flavonoids from Rhizoma Polygoni Multiflori by Macroporous Adsorption Resin. Clinical Practice. Dec. 31, 2008;1(9):720-723.
Yoshida et al., Diglucuronoflavones from purple leaves of Perilla ocimoides. Phytochemistry. Jul. 1993;33(4):917-9.
Chinese Office Action for Application No. 201580011098.3, dated Sep. 30, 2018, 11 pages.
Chinese Office Action for Application No. 201580011098.3, dated Sep. 10, 2019, 13 pages.
European Office Action for Application No. 15765481.5, dated Jul. 22, 2019, 5 pages.
International Search Report and Written Opinion for Application No. PCT/CN2015/074366, dated Apr. 9, 2015, 16 pages.
Japanese Office Action for Application No. 2017-500116, dated Dec. 4, 2018, 13 pages.

(Continued)

*Primary Examiner* — Russell G Fiebig
(74) *Attorney, Agent, or Firm* — McCarter & English, LLP; Steven G. Davis; Wei Song

(57) ABSTRACT

Disclosed is a *Glechoma longituba* (Nakai) Kupr. extract, specifically compounds I and II, a preparation method for same, and a use thereof in preparing a medicament for blood glucose decease, blood lipids decrease, weight loss, and kidney disease treatment or a method for treatment of said diseases, and a composition containing the extract.

25 Claims, 12 Drawing Sheets

(56) References Cited

OTHER PUBLICATIONS

Japanese Office Action for Application No. 2017-500116, dated May 24, 2019, 6 pages.

(A) Measurement results of inhibition activity of individual compounds against DDP4

| Compound name | Inhibition rate (%) | |
|---|---|---|
| | 100μM | 10μM |
| Compound I | 40.82±3.26 | 13.52±0.62 |
| Compound II | 34.09±3.91 | 15.85±2.13 |

(C) Compound I & Compound II OGTT-AUC (B) Compound I & Compound II Acute OGTT

- Control group
- Calibration group
- Compound I 100mg/kg
- Compound I 200mg/kg
- Compound II 100mg/kg
- Compound II 200mg/kg
- Sitagliptin 10mg/kg

GLECHOMA LONGITUBE EXTRACT, PREPARATION METHOD FOR SAME, AND USE THEREOF IN SUGAR REDUCTION, WEIGHT LOSS, AND LIPID REDUCTION

This application is the U.S. National Phase of, and Applicant claims priority from, International Patent Application No. PCT/CN2015/074366, filed on Mar. 17, 2015, which claims priority from Chinese Application No. 201410104913.8, filed on Mar. 17, 2014, each of which is incorporated herein by reference.

TECHNICAL FIELD

The present invention pertains to the technical field of medicine. The present invention discloses an extract of *Glechoma longituba* (Nakai) Kupr. for decreasing blood glucose, decreasing blood lipids, losing weight, or treating kidney diseases, a method of preparing the same, use of the same in the manufacture of medicament for decreasing blood glucose, decreasing blood lipid, losing weight, or treating kidney diseases, or a method of using the same for treating said diseases, and a composition comprising the extract. The present invention also discloses Compound I and Compound II for decreasing blood glucose, decreasing blood lipids, losing weight, or treating kidney diseases, a method of preparing the same, use of the same in the manufacture of medicament for decreasing blood glucose, decreasing blood lipid, losing weight, or treating kidney diseases, or a method of using the same for treating said diseases, and a composition comprising the compounds.

TECHNICAL BACKGROUND

Diabetes mellitus (DM) is a systemic metabolic disorder characterized in elevated blood glucose resulted from insulin secretion defect and (or) the dysfunction of insulin in normal physiological action. Modern medicine research found that there is an explicit epidemiological link between elevated blood lipids and diabetes mellitus. Regulation of blood lipids for overweight people can prevent high blood glucose. Reduction of body weight and regulation of blood lipids for diabetic patients are keys to decrease mortality and disability rate of diabetic patients.

*Glechoma longituba* (Nakai) Kupr., also known as HuoXueDan or TouGuXiao, is dried whole plant of *Glechoma* Linn., Labiatae, widely distributed over temperate region of Eurasia and also cultivated in south and north Americas. In our country, it is distributed in various parts of the country except for northwest and inner mongolia. *Glechoma longituba* (Nakai) Kupr. was firstly recited in Bencao Gangmu Shiyi, tastes bitter and pungent, has cool nature, is attributed to channels of liver, kidney, and bladder, and has effects on promoting diuresis and treating stranguria, clearing heat and detoxifying, dissipating stasis and eliminating swelling. Clinically, *Glechoma longituba* (Nakai) Kupr. is mainly used for treating urinary stone, hepatic and cystic stone, damp-heat jaundice, and injury due to falling. Chinese Pharmacopeia (2010 edition) lists HuoXueDan, *Glechoma longituba* (Nakai) Kupr., Labiate plant, as the source of *Glechoma longituba* (Nakai) Kupr. medical material.

It was reported that the total flavones in a 65% ethanol extract of *Glechoma longituba* (Nakai) Kupr. can decrease the blood glucose level in diabetic mouse induced by streptozotocin, and it was believed that the glucose-decreasing mechanism is to inhibit pancreatic islet β-cell damage induced by streptozotocin, thereby increasing β-cell number in diabetic mouse induced by streptozotocin (Yuan Chunlin, et al., *Pharmacology and Clinics of Chinese Materia Medica*, 2008, 24(3), 57-58). Yang Nianyun, et al., (*Journal of China Pharmaceutical University*, 2005, 36(3), 210-212) obtained 10 *Glechoma longituba* (Nakai) Kupr. flavone compounds from a 80% ethanol extract of *Glechoma longituba* (Nakai) Kupr. by means of extraction and column chromatography; after that, Yang Nianyun, et al., (*Chinese Journal of Natural Medicines*, 2006, 4(2), 98-100) separated 10 compounds again from a n-butanol extraction fraction of a 80% ethanol reflux extract liquid of *Glechoma longituba* (Nakai) Kupr., wherein the yield of Compound II is merely about 2 ppm. None of Yuan Chunling, et al., and Yang Nianyun, et al., reported the antidiabetic activity of any specific flavone compound in the extract of *Glechoma longituba* (Nakai) Kupr. Meanwhile, the ingredients of the total flavones reported by Yuan Chunling, et al., and Yang Nianyun, et al., do not comprise luteolin-7-O-[β-glucuronosyl(1→2)β-glucuronic acid] of the present invention.

Japanese researchers once studied acute reduction of glucose by a water decoction of *Glechoma hederacea* subsp. *grandis* in an in vivo assay of animals (Shinji I., et al. Nippon Shokuhin Kagaku Kogaku Kaishi, 2007, 54(9):412-414). This reference presumed that the polysaccharide ingredients in the resulting extract liquid of *Glechoma hederacea* subsp. *grandis* are the primary active components for decreasing glucose. However, the Chinese Pharmacopoeia (2010 edition) does not list *Glechoma hederacea* subsp. *grandis* as a source of the traditional Chinese medicine, *Glechoma longituba* (Nakai) Kupr. Moreover, the Flora of China (Editorial board of Flora of China of Chinese Academy of Sciences, *Flora of China* (Volume 65, Fascicle 2), Beijing: Science Press, 1977) specifically lists *Glechoma hederacea* subsp. *grandis* as a separate variety of *Glechoma* Linn., indicating that *Glechoma hederacea* subsp. *grandis* and *Glechoma longituba* (Nakai) Kupr. (*Glechoma longituba* (Nakai) Kupr.) do not belong to the same variety.

SUMMARY OF INVENTION

The present invention aims at providing an extract of *Glechoma longituba* (Nakai) Kupr. for decreasing blood glucose, decreasing blood lipid, losing weight, or treating kidney diseases, a method of preparing the same, use of the same in the manufacture of medicament for decreasing blood glucose, decreasing blood lipid, losing weight, or treating kidney diseases, or a method of using the same for treating said diseases, and a composition comprising the extract. The present invention also aims at providing Compounds I and II for decreasing blood glucose, decreasing blood lipid, losing weight, or treating kidney diseases, a method of preparing the same, use of the same in the manufacture of medicament for decreasing blood glucose, decreasing blood lipid, losing weight, or treating kidney diseases, or a method of using the same for treating said diseases, and a composition comprising the compounds.

The present invention provides an extract of *Glechoma longituba* (Nakai) Kupr. comprising:

Compound I, luteolin-7-O-[β-glucuronosyl(1→2)β-glucuronic acid]

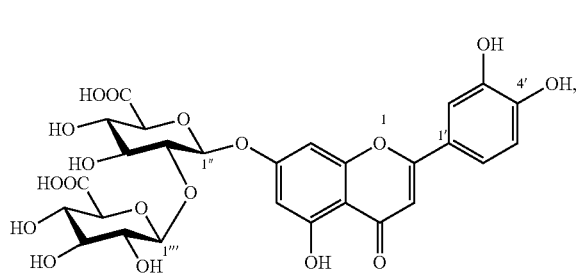

and

Compound II, apigenin-7-O-[β-glucuronosyl(1→2)β-glucuronic acid]

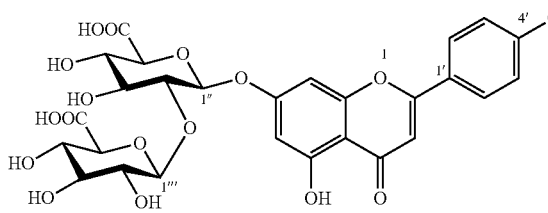

and the weight of both Compound I and Compound II account for 1%-75%, preferably 1%-25%, 20%-60%, or 50%-75%, of the total weight of the extract.

In one preferred aspect, both Compound I and Compound II comprised in the extract of *Glechoma longituba* (Nakai) Kupr. of the present invention account for no less than 1%, 2%, 3%, 4%, 5%, 6%, 7%, 8%, 9%, 10%, 15%, 20%, 21%, 22%, 23%, 24%, 25%, 26%, 27%, 28%, 29%, 30%, 35%, 40%, 45%, 50%, 51%, 52%, 53%, 54%, 55%, 56%, 57%, 58%, 59%, 60%, 65%, 70%, 71%, 72%, 73%, 74%, 75%, 76%, 77%, 78%, 79%, 80%, 85%, 90%, 95%, 99% of the total weight of the extract. In still preferred aspect, both Compound I and Compound II comprised in the extract of *Glechoma longituba* (Nakai) Kupr. of the present invention account for no more than 99%, 95%, 90%, 85%, 80%, 79%, 78%, 77%, 76%, 75%, 74%, 73%, 72%, 71%, 70%, 65%, 60%, 59%, 58%, 57%, 56%, 55%, 54%, 53%, 52%, 51%, 50%, 45%, 40%, 35%, 30%, 29%, 28%, 27%, 26%, 25%, 24%, 23%, 22%, 21%, 20%, 15%, 10%, 9%, 8%, 7%, 6%, 5%, 4%, 3%, 2%, 1% of the total weight of the extract. In still another preferred aspect, both Compound I and Compound II comprised in the extract of *Glechoma longituba* (Nakai) Kupr. of the present invention account for a weight content in the range of any combination of the above values of weight content, such as, 1%-99%, 1%-25%, 25%-50%, 50%-75%, 75%-99%, 25%-99%, 25%-75%, 50%-99%, 1%-75%, 1%-25%, 20%-60%, 50%-75%, and the like, of the total weight of the extract. The ranges as set forth in the invention include or exclude endpoints.

The present invention also provides an extract of *Glechoma longituba* (Nakai) Kupr. comprising:

Compound I, luteolin-7-O-[β-glucuronosyl(1→2)β-glucuronic acid]

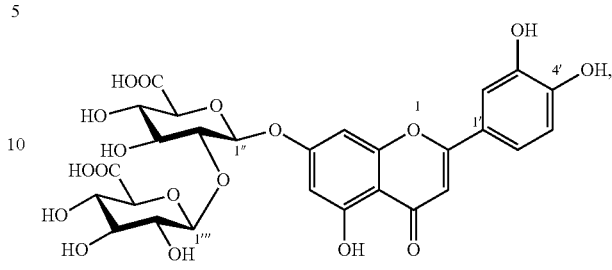

and

Compound II, apigenin-7-O-[β-glucuronosyl(1→2)β-glucuronic acid]

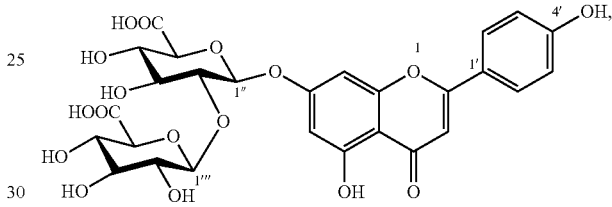

and
the extract of *Glechoma longituba* (Nakai) Kupr. is obtained by a method comprising:
a) extracting *Glechoma longituba* (Nakai) Kupr. with an aqueous solution one or more times to obtain an aqueous extract liquid of *Glechoma longituba* (Nakai) Kupr., and, optionally, concentrating the resulting extract liquid;
b) adding to the optionally concentrated aqueous extract liquid of *Glechoma longituba* (Nakai) Kupr. a volume of an alcoholic solution to generate a precipitate; and
c) separating the precipitate generated in step b).

In one aspect of the present invention, any extract of *Glechoma longituba* (Nakai) Kupr. of the present invention comprises Compound I in a content of more than 0.6%, preferably more than 25%, more preferably more than 39%, and Compound II in a content of more than 0.6%, preferably more than 25%, more preferably more than 32%.

The present invention also provides:
a mixture comprising

Compound I, luteolin-7-O-[β-glucuronosyl(1→2)β-glucuronic acid]

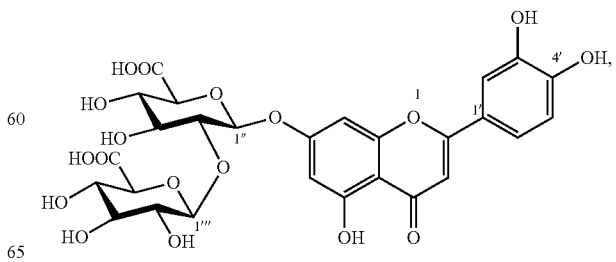

or a pharmaceutically acceptable salt thereof; and/or

Compound II, apigenin-7-O-[β-glucuronosyl(1→2) β-glucuronic acid]

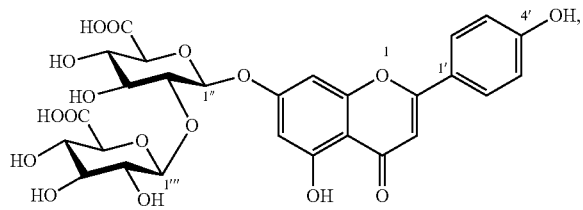

or a pharmaceutically acceptable salt thereof;
and/or both Compound I and Compound II or any pharmaceutically acceptable salt of the both compounds.

In another aspect of the present invention, the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, comprises Compound I in a content of more than 0.6%, preferably more than 25%, more preferably more than 39%, and Compound II in a content of more than 0.6%, preferably more than 25%, more preferably more than 32%.

In one preferred aspect, the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, comprises Compound I or Compound II in a content of no less than 1%, 2%, 3%, 4%, 5%, 6%, 7%, 8%, 9%, 10%, 15%, 20%, 21%, 22%, 23%, 24%, 25%, 26%, 27%, 28%, 29%, 30%, 35%, 40%, 45%, 50%, 51%, 52%, 53%, 54%, 55%, 56%, 57%, 58%, 59%, 60%, 65%, 70%, 71%, 72%, 73%, 74%, 75%, 76%, 77%, 78%, 79%, 80%, 85%, 90%, 95%, 99%, respectively. In still preferred aspect, the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, comprises Compound I or Compound II in a content of no more than 99%, 95%, 90%, 85%, 80%, 79%, 78%, 77%, 76%, 75%, 74%, 73%, 72%, 71%, 70%, 65%, 60%, 59%, 58%, 57%, 56%, 55%, 54%, 53%, 52%, 51%, 50%, 45%, 40%, 35%, 30%, 29%, 28%, 27%, 26%, 25%, 24%, 23%, 22%, 21%, 20%, 15%, 10%, 9%, 8%, 7%, 6%, 5%, 4%, 3%, 2%, 1%, respectively. In still another preferred aspect, the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, comprises Compound I or Compound II in a content in the range of any combination of the above values of weight content, such as, 1%-99%, 1%-25%, 25%-50%, 50%-75%, 75%-99%, 25%-99%, 25%-75%, 50%-99%, 1%-75%, 1%-25%, 20%-60%, 50%-75%, and the like. The ranges as set forth in the invention include or exclude endpoints.

In one aspect of the present invention, the present invention provides a pharmaceutical composition comprising any extract of Glechoma longituba (Nakai) Kupr. of the present invention and a pharmaceutically acceptable carrier. In another aspect of the present invention, the present invention also provides a pharmaceutical composition comprising the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, and a pharmaceutically acceptable carrier.

In one aspect of the present invention, Compound I and Compound II in the pharmaceutical composition comprising any extract of Glechoma longituba (Nakai) Kupr. of the present invention account for more than 50% of the total weight of active ingredients in the pharmaceutical composition; or, the biological activity of the pharmaceutical composition such as DPP4 inhibition activity decreases more than 50% after Compounds I and II are substantially removed from the pharmaceutical composition comprising the extract. In another aspect of the present invention, Compound I and Compound II in the pharmaceutical composition comprising the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, account for more than 50% of the total weight of active ingredients in the pharmaceutical composition; or, the biological activity of the pharmaceutical composition such as DPP4 inhibition activity decreases more than 50% after Compounds I and II are substantially removed from the pharmaceutical composition comprising the mixture.

In one aspect of the present invention, the contents of caffeic acid and rosmarinic acid in any extract of Glechoma longituba (Nakai) Kupr. of the present invention are less than 0.5%, preferably less than 0.1%. In another aspect of the present invention, the contents of caffeic acid and rosmarinic acid in the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds are less than 0.5%, preferably less than 0.1%.

In one aspect of the present invention, the present invention discloses that any of the extract of Glechoma longituba (Nakai) Kupr. has activities of decreasing blood glucose, decreasing blood lipid, losing weight, or treating kidney diseases. In another aspect of the present invention, the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds, has activities of decreasing blood glucose, decreasing blood lipid, losing weight, or treating kidney diseases.

Accordingly, the present invention provides an extract for decreasing blood glucose, decreasing blood lipid, losing weight, or treating kidney diseases. In another aspect of the present invention, the present invention also provides a mixture comprising Compound I or a pharmaceutically acceptable salt thereof, and/or Compound II or a pharmaceutically acceptable salt thereof, and/or both Compound I and Compound II or any pharmaceutically acceptable salt of the both compounds for decreasing blood glucose, decreasing blood lipid, losing weight, or treating kidney diseases.

Optionally, the present invention provides a method of decreasing blood glucose, decreasing blood lipid, losing weight, or treating kidney diseases, comprising administrating any extract of *Glechoma longituba* (Nakai) Kupr. of the present invention to a patient in need thereof. In another aspect of the present invention, the present invention provides a method of decreasing blood glucose, decreasing blood lipid, losing weight, or treating kidney diseases, comprising administrating the mixture of the present invention comprising Compound I or a pharmaceutically acceptable salt thereof, and/or Compound II or a pharmaceutically acceptable salt thereof, and/or both Compound I and Compound II or any pharmaceutically acceptable salt of the both compounds to a patient in need thereof.

Or still optionally, the present invention provides use of any of the said extract of *Glechoma longituba* (Nakai) Kupr. in the manufacture of medicament for decreasing blood glucose, decreasing blood lipid, losing weight, or treating kidney diseases. The present invention also provides use of the said mixture comprising Compound I or a pharmaceutically acceptable salt thereof, and/or Compound II or a pharmaceutically acceptable salt thereof, and/or both Compound I and Compound II or any pharmaceutically acceptable salt of the both compounds in the manufacture of medicament for decreasing blood glucose, decreasing blood lipid, losing weight, or treating kidney diseases.

The present invention also provides a method of extracting *Glechoma longituba* (Nakai) Kupr., comprising:
a) extracting *Glechoma longituba* (Nakai) Kupr. with an aqueous solution one or more times to obtain an aqueous extract liquid of *Glechoma longituba* (Nakai) Kupr., and, optionally, concentrating the resulting extract liquid;
b) adding to the optionally concentrated aqueous extract liquid of *Glechoma longituba* (Nakai) Kupr. a volume of an alcoholic solution to generate a precipitate; and
c) separating the precipitate generated in step b).

In one aspect of the present invention, the aqueous solution in step a) of the method of extracting *Glechoma longituba* (Nakai) Kupr. of the present invention has a water content of more than 40%, preferably more than 80%, and most preferably, the aqueous solution is water.

In one aspect of the present invention, the extraction in step a) of the method of extracting *Glechoma longituba* (Nakai) Kupr. of the present invention is heating reflux or ultrasonic extraction, preferably, performed 2 to 5 times.

In one aspect of the present invention, the aqueous extract liquid of *Glechoma longituba* (Nakai) Kupr. obtained in step a) of the method of extracting *Glechoma longituba* (Nakai) Kupr. of the present invention can also be optionally extracted by an organic solvent, the organic phase is discarded, and the treated aqueous extract liquid of *Glechoma longituba* (Nakai) Kupr. is left for further operation, wherein the organic solvent is preferably ethyl acetate or dichloromethane.

In one aspect of the present invention, the aqueous extract liquid of *Glechoma longituba* (Nakai) Kupr. obtained in step a) of the method of extracting *Glechoma longituba* (Nakai) Kupr. of the present invention can be further refrigerated, preferably at 4-6° C., after optional concentration, preferably under reduced pressure.

In one aspect of the present invention, the alcoholic solution in step b) of the method of extracting *Glechoma longituba* (Nakai) Kupr. of the present invention is preferably a mixed system of ethanol-water, more preferably 90% ethanol, and most preferably 95% ethanol.

In one aspect of the present invention, the alcoholic solution in step b) of the method of extracting *Glechoma longituba* (Nakai) Kupr. of the present invention has a volume of 2-4 times of that of the optionally concentrated aqueous extract liquid of *Glechoma longituba* (Nakai) Kupr.

In one aspect of the present invention, the precipitate obtained by separation in step c) of the method of extracting *Glechoma longituba* (Nakai) Kupr. of the present invention can be optionally lyophilized.

In one aspect of the present invention, the precipitate obtained by separation in step c) of the method of extracting *Glechoma longituba* (Nakai) Kupr. of the present invention can be optionally purified with a macroporous adsorption resin, wherein the purification with a macroporous adsorption resin is performed by:
i) dissolving the precipitate obtained by separation in step c) with an aqueous solvent to prepare an aqueous solution, and, optionally, removing the residual alcohol;
ii) adding onto the macroporous resin the aqueous solution from which the residual alcohol is optionally removed;
iii) removing components of proteins and polysaccharides with an aqueous eluent; and
iv) eluting with an alcoholic eluent and concentrating the resulting eluate to produce a purified extract of *Glechoma longituba* (Nakai) Kupr.

In one aspect of the present invention, the aqueous solution in step i) of the present invention has a water content of more than 40%, preferably more than 80%, and most preferably, the aqueous solution is water.

In one aspect of the present invention, the macroporous resin in step ii) of the present invention is D-101, D-101-I, DA-201, DM-301, DM-130, AB-8, HPD-100, HPD-300, HPD-400, HPD-600, HPD-826, or fillers similar to these resins, preferably D-101.

In one aspect of the present invention, the aqueous solution in step iii) of the present invention has a water content of more than 90%, preferably more than 95%, and most preferably, the aqueous solution is water.

In one aspect of the present invention, the alcoholic eluent in step iv) of the present invention is a mixed system of ethanol-water, preferably 5-20% ethanol, and most preferably 10-15% ethanol.

The present invention provides preferred process of preparing individual Compound I and Compound II, characterized in that the extract of *Glechoma longituba* (Nakai) Kupr. as obtained through steps i) to iv) of the present invention, can be rapidly separated and purified by means of column chromatography using polyamides, silica gels, gels, or reverse phase packing as fillers, preferably, reverse phase packing, to achieve purities of an individual Compounds that are up to 96% or above.

The pharmaceutical composition of the present invention is in form of tablets, hard capsules, soft capsules, enteric capsule, microcapsules, granules, syrups, injections, granules, emulsions, suspensions, solutions, and sustained-release formulations for oral or non-oral administration.

The pharmaceutically acceptable carriers of the present invention refer to pharmaceutically acceptable carriers well-known to those skilled in the art. The pharmaceutically acceptable carriers of the present invention include, but are not limited to, fillers, humectants, adhesives, disintegrating agents, lubricants, binders, glidants, flavoring agents, surfactants, preservatives, and the like. The fillers include, but are not limited to, lactose, microcrystalline celluloses, starch, powdered sugar, dextrin, mannitol, calcium sulfate, and the like. The humectants and binders include, but are not limited to, sodium carboxymethyl cellulose, hydroxypropyl cellulose, hydroxypropylmethyl cellulose, gelatin, sucrose, polyvinylpyrrolidone, and the like. The disintegrating agents include, but are not limited to, sodium carboxymethyl starch, crosslinked polyvinylpyrrolidone, crosslinked sodium carboxymethyl cellulose, lower substituted hydroxypropyl cellulose, and the like. The lubricants include, but are not limited to, magnesium stearate, micro powder silica gel, talc, hydrogenated vegetable oil, polyethylene glycol, magnesium lauryl sulfate, and the like. The binders include, but are not limited to, acacia, alginic acid, calcium carboxymethyl cellulose, sodium carboxymethyl cellulose, dextrates, dextrin, dextrose, ethylcellulose, gelatin, liquid glucose, guar gum, hydroxyethyl cellulose, hydroxypropyl cellulose, hydroxypropylmethyl cellulose, magnesium aluminum silicate, maltodextrin, methylcellulose, polymethacrylates, polyvinylpyrrolidone, pregelatinized starch, sodium alginate, sorbitol, starch, syrup, and tragacanth. The glidants include, but are not limited to, colloidal silicon dioxide, powdered cellulose, magnesium trisilicate, silicon dioxide, and talc. The flavoring agents include, but are not limited to, aspartame, stevioside, fructose, glucose, syrup, honey, xylitol, mannitol, lactose, sorbitol, maltitol, glycyrrhizin. The surfactants include, but are not limited to, Tween-80, poloxamer. The preservatives include, but are not limited to, paraben, sodium benzoate, potassium sorbate, and the like.

The pharmaceutically acceptable salts of the present invention include, but are not limited to, salts formed with inorganic acids, such as, hydrochloric acid, hydrobromic acid, hydrofluoric acid, sulfuric acid, nitric acid, phosphoric acid; acid addition salts formed with organic acids, such as, formic acid, acetic acid, propionic acid, oxalic acid, malonic acid, succinic acid, fumaric acid, maleic acid, lactic acid, malic acid, tartaric acid, citric acid, picric acid, methanesulfonic acid, ethanesulfonic acid, and with acidic amino acids, such as aspartic acid, glutamic acid; or salts formed with bases, for example, inorganic bases, such as, sodium, potassium; or base addition salts formed with basic amino acids, such as, lysine, arginine, ornithine.

The *Glechoma longituba* (Nakai) Kupr. (*Glechoma longituba* (Nakai) Kupr.) of the present invention, also known as HuoXueDan or TouGuXiao, is dried whole plant of Labiatae *Glechoma* Linn., and is the only legal source variety of *Glechoma longituba* (Nakai) Kupr. medicinal material in Chinese Pharmacopoeia (2010 edition). *Glechoma* Linn. further includes varieties, such as, *Glechoma hederacea* Linn., *Glechoma biondiana* (Diels) C. Y. Wu & C. Chen, and *Glechoma sinograndis* C. Y. Wu. These varieties have the similar efficiency as *Glechoma longituba* (Nakai) Kupr.

The dipeptidyl peptidase IV (DDP4) of the present invention is a transmembrane serine protein, a member of prolyl oligopeptidase family. DDP4 is a novel target for the treatment of diabetes mellitus type 2. It is one of the key enzymes primarily promoting the degradation and inactivation of glucagon-like peptide-1 (GLP-1) in vivo and in vitro. At present, it has been medically demonstrated that DDP4 inhibitor is a novel antidiabetic medicament. Clinical outcomes showed that this type of medicament has good effect on decreasing blood glucose without observation of common adverse reactions such as weight gain and hypoglycemia resulted from antidiabetic medicaments of insulin or sulfonylureas, and thus, studies with respect to DDP4 inhibitors have become a hotspot of antidiabetic medicament research.

The present invention finds that Compound I and Compound II can effectively inhibit DDP4 activity, where the inhibition rates for DDP4 at the concentration of 100 μM are 40.8% and 34.1%, respectively, and thus have blood glucose-decreasing effect.

Accordingly, the present invention provides an extract for decreasing blood glucose. In another aspect of the present invention, the present invention also provides a mixture comprising Compound I or a pharmaceutically acceptable salt thereof, and/or Compound II or a pharmaceutically acceptable salt thereof, and/or pharmaceutically acceptable salts of Compounds I and II or any of the both for decreasing blood glucose. Optionally, the present invention provides a method of decreasing blood glucose, comprising administrating any extract of *Glechoma longituba* (Nakai) Kupr. of the present invention to a patient in need thereof. In another aspect of the present invention, the present invention provides a method of decreasing blood glucose, decreasing blood lipid, losing weight, or treating kidney diseases, comprising administrating the mixture of the present invention comprising Compound I or a pharmaceutically acceptable salt thereof, and/or Compound II or a pharmaceutically acceptable salt thereof, and/or pharmaceutically acceptable salts of Compounds I and II or any of the both to a patient in need thereof. Or still optionally, the present invention provides use of any of the extract of *Glechoma longituba* (Nakai) Kupr. in the manufacture of medicament for decreasing blood glucose. The present invention also provides use of the mixture comprising Compound I or a pharmaceutically acceptable salt thereof, and/or Compound II or a pharmaceutically acceptable salt thereof, and/or pharmaceutically acceptable salts of Compounds I and II or any of the both in the manufacture of medicament for decreasing blood glucose. The present invention also provides use of any of the extract of *Glechoma longituba* (Nakai) Kupr. in the manufacture of medicament for the inhibition of DDP4 activity. The present invention also provides use of the mixture comprising Compound I or a pharmaceutically acceptable salt thereof, and/or Compound II or a pharmaceutically acceptable salt thereof, and/or pharmaceutically acceptable salts of Compounds I and II or any of the both in the manufacture of medicament for the inhibition of DDP4 activity. In one aspect of the present invention, the inhibition of activity of dipeptidyl peptidase IV of the present invention refers to the treatment of diabetes mellitus.

Glucose oxidase (GOX) is an oxidase with flavin adenine mononucleotide (FMN) as auxiliary group, which catalyzes the oxidation of glycollic acid to oxalic acid. Overexpression of GOX would promote the production of oxalate, thereby increasing risks of kidney calculi and nephritis. Therefore, it has been an important method and approach to seek inhibitors of glucose oxidase for the development of a medicament for treating kidney calculi and nephritis. The present invention further finds that Compound I and Compound II have a certain inhibitory activity for GOX, where $IC_{50}$ value of Compound I is 0.5 mM and $IC_{50}$ value of Compound II is 0.4 mM, and thus have potential pharmacological activity for the treatment of kidney calculi and nephritis.

Accordingly, the present invention provides an extract for treating kidney diseases. In another aspect of the present invention, the present invention also provides a mixture comprising Compound I or a pharmaceutically acceptable salt thereof, and/or Compound II or a pharmaceutically acceptable salt thereof, and/or pharmaceutically acceptable salts of Compounds I and II or any of the both for treating kidney diseases. Optionally, the present invention provides a method of treating kidney diseases, comprising administrating any extract of *Glechoma longituba* (Nakai) Kupr. of the present invention to a patient in need thereof. In another aspect of the present invention, the present invention provides a method of decreasing blood glucose, decreasing blood lipid, losing weight, or treating kidney diseases, comprising administrating the mixture of the present invention comprising Compound I or a pharmaceutically acceptable salt thereof, and/or Compound II or a pharmaceutically acceptable salt thereof, and/or pharmaceutically acceptable salts of Compounds I and II or any of the both to a patient in need thereof. Or still optionally, the present invention provides use of any of the extract of *Glechoma longituba* (Nakai) Kupr. in the manufacture of medicament for treating kidney diseases. The present invention also provides use of the mixture comprising Compound I or a pharmaceutically acceptable salt thereof, and/or Compound II or a pharmaceutically acceptable salt thereof, and/or pharmaceutically acceptable salts of Compounds I and II or any of the both in the manufacture of medicament for treating kidney diseases.

Triglyceride (also known as triacylglycerol) is the primary form for storing energy in eucaryote. In mammals, triglyceride is mainly synthesized in small intestine, liver, and adipocytes. Metabolism of triglyceride, disorder and dysfunction of both absorption and de novo synthesis, relates to pathogenesis of several diseases, for example, obesity, hyperlipidemia, and the like. Pancrelipase is secreted by pancreatic acinar cells, enters duodenum through pancreatic duct, and hydrolyzes triglyceride as absorbable 2-monoacylglycerol and free fat acids at the oil-water interface of duodenum and upper small intestine. Pancrelipase is responsible for the hydrolysis of 50% to 70% dietary fat. The inhibition of activity of pancrelipase can prevent intestinal triacylglycerol from digestion and absorption, lower the level of blood triglyceride, and reduce the aggregation of tissue fats, and thus can have an effect on decreasing blood lipid and losing weight. Diacylglycerol acyltransferase 1 (DGAT1) catalyzes the last step of triacylglycerol synthesis, the transfer of acyl of acyl coenzyme A to 2-monoacylglycerol to form triacylglycerol, and is the rate-limiting enzyme of triacylglycerol synthesis. The synthesis of triglyceride from biacylglycerol can be reduced by the inhibition or reduction of DGAT1 enzyme activity. Inhibitors of DGAT1 enzyme can be used to treat diseases associated with abnormal metabolism of triglyceride, for example, having an effect on decreasing blood lipid and losing weight.

The present invention also finds that Compound I and Compound II act to inhibit absorption of fats in foods, thereby functioning to lower blood lipid and lose weight. The present invention finds that Compound I and Compound II can effectively inhibitor activities of DGAT1 and pancrelipase, thereby functioning to lower blood lipid and lose weight. Compounds I and II at concentrations of 50 μM both have inhibition rates for DGAT1 of more than 50%; Compounds I and II at concentrations of 10 μM still exhibit about 20% inhibitory activity for DGAT1. Compounds I and II at the same concentration both have inhibition rates for pancrelipase of more than 40%.

Accordingly, the present invention provides an extract for decreasing blood lipid. In another aspect of the present invention, the present invention also provides a mixture comprising Compound I or a pharmaceutically acceptable salt thereof, and/or Compound II or a pharmaceutically acceptable salt thereof, and/or pharmaceutically acceptable salts of Compounds I and II or any of the both for decreasing blood lipid. Optionally, the present invention provides a method of decreasing blood lipid, comprising administrating any extract of *Glechoma longituba* (Nakai) Kupr. of the present invention to a patient in need thereof. In another aspect of the present invention, the present invention provides a method of decreasing blood glucose, decreasing blood lipid, losing weight, or treating kidney diseases, comprising administrating the mixture of the present invention comprising Compound I or a pharmaceutically acceptable salt thereof, and/or Compound II or a pharmaceutically acceptable salt thereof, and/or pharmaceutically acceptable salts of Compounds I and II or any of the both to a patient in need thereof. Or still optionally, the present invention provides use of any of the extract of *Glechoma longituba* (Nakai) Kupr. in the manufacture of medicament for decreasing blood lipid. The present invention also provides use of the mixture comprising Compound I or a pharmaceutically acceptable salt thereof, and/or Compound II or a pharmaceutically acceptable salt thereof, and/or pharmaceutically acceptable salts of Compounds I and II or any of the both in the manufacture of medicament for decreasing blood lipid.

Accordingly, the present invention provides an extract for losing weight. In another aspect of the present invention, the present invention also provides a mixture comprising Compound I or a pharmaceutically acceptable salt thereof, and/or Compound II or a pharmaceutically acceptable salt thereof, and/or pharmaceutically acceptable salts of Compounds I and II or any of the both for losing weight. Optionally, the present invention provides a method of losing weight, comprising administrating any extract of *Glechoma longituba* (Nakai) Kupr. of the present invention to a patient in need thereof. In another aspect of the present invention, the present invention provides a method of decreasing blood glucose, decreasing blood lipid, losing weight, or treating kidney diseases, comprising administrating the mixture of the present invention comprising Compound I or a pharmaceutically acceptable salt thereof, and/or Compound II or a pharmaceutically acceptable salt thereof, and/or pharmaceutically acceptable salts of Compounds I and II or any of the both to a patient in need thereof. Or still optionally, the present invention provides use of any of the extract of *Glechoma longituba* (Nakai) Kupr. in the manufacture of medicament for losing weight. The present invention also provides use of the mixture comprising Compound I or a pharmaceutically acceptable salt thereof, and/or Compound II or a pharmaceutically acceptable salt thereof, and/or pharmaceutically acceptable salts of Compounds I and II or any of the both in the manufacture of medicament for losing weight.

The diabetes mellitus of the present invention include diabetes mellitus type 1, diabetes mellitus type 2, other special types of diabetes mellitus and gestational diabetes mellitus.

The decrease of blood lipids of the present invention refers to the decease of triglyceride level in blood.

The treatment of kidney diseases of the present invention refers to the treatment of kidney calculi, nephritis, and the like.

The present invention will illustrate the beneficial effect of the present invention by means of examples in below. Those skilled in the art will recognize that these examples are illustrative but not limiting. These examples will not limit the scope of the present invention in any way.

Kupr. of the present invention and in the extract as obtained by the extraction process reported by references.

Figure 3:
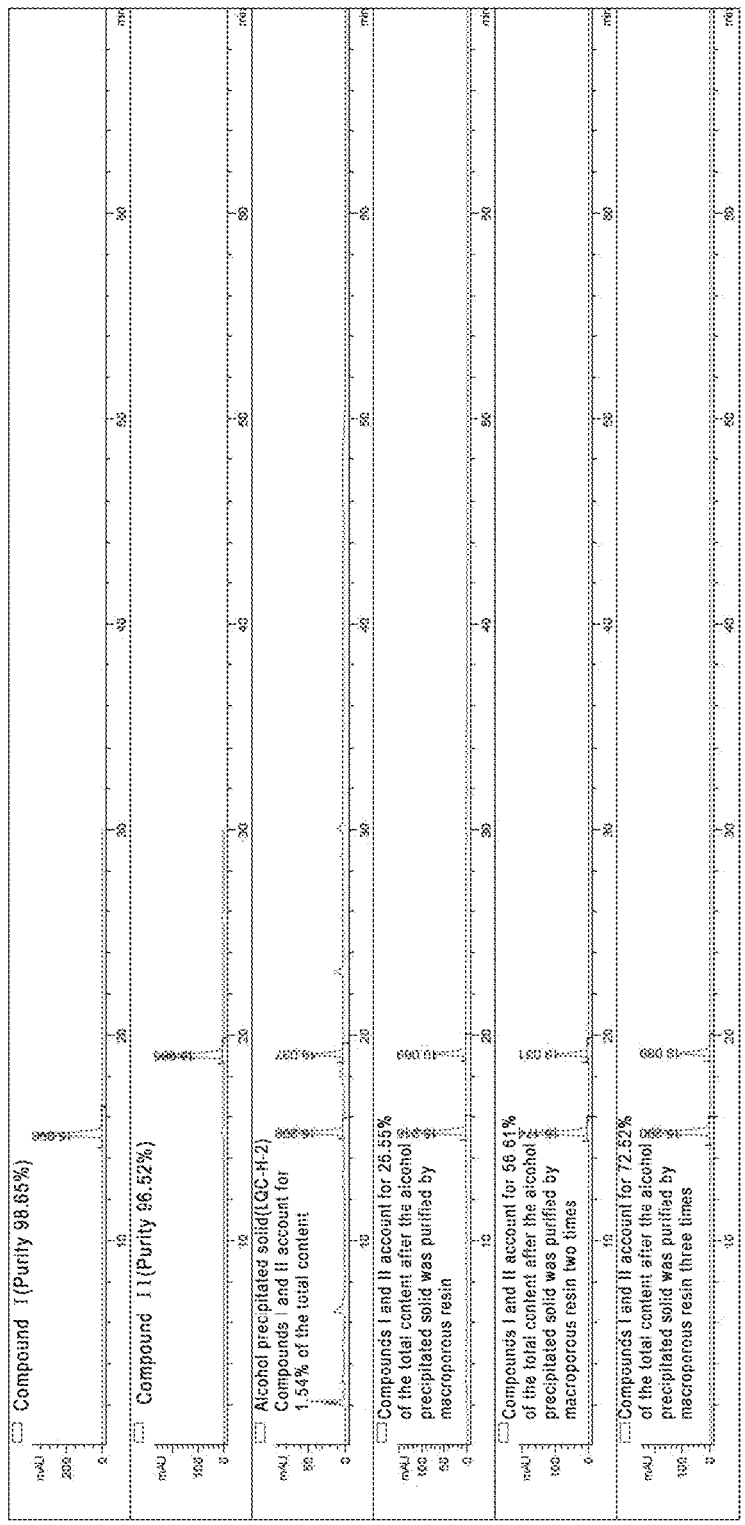

FIG. 3 shows the HPLC analysis results of Compounds I and II in the extract of *Glechoma longituba* (Nakai) Kupr. as prepared by the preferred preparation processes.

Figure 4:
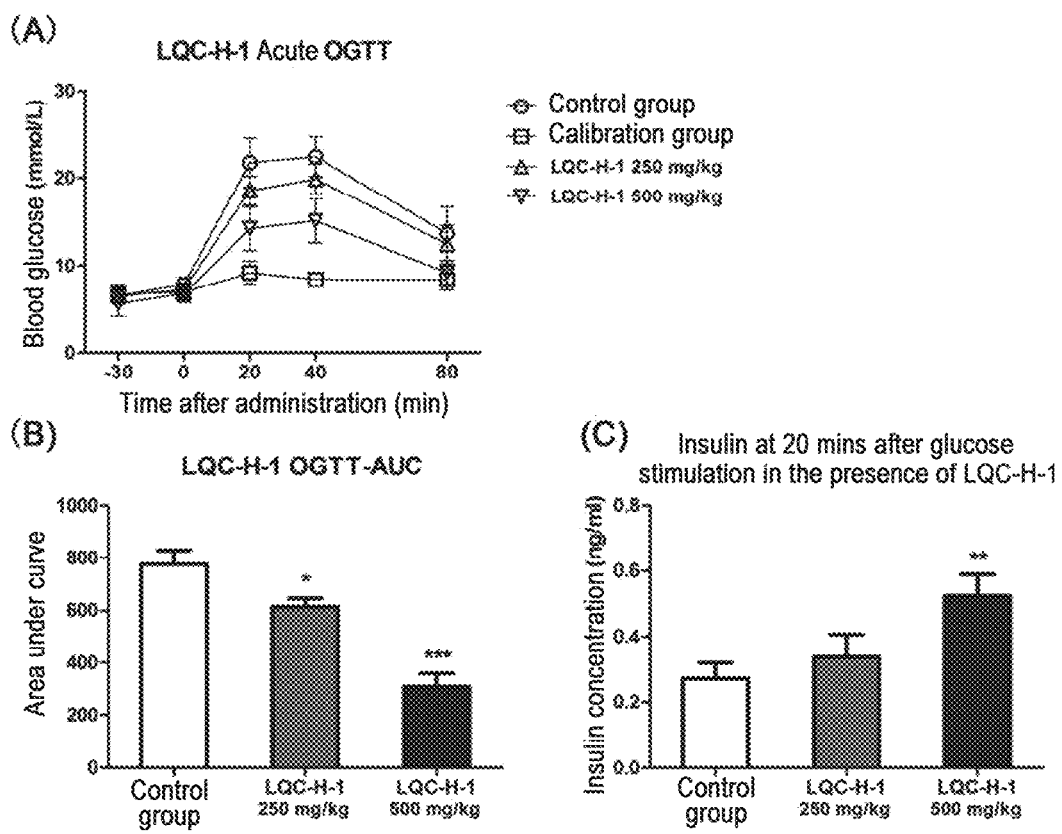

FIG. 4 shows that the extracts of *Glechoma longituba* (Nakai) Kupr., LQC-H-1, at both 250 mg/kg and 500 mg/kg could significantly enhance acute oral glucose tolerance in mice and increased blood insulin level in mice after oral administration of glucose. Note: FIG. 4 (A): LQC-H-1 enhanced acute oral glucose tolerance in mice, where the abscissa is time after administration of glucose and the ordinate is blood glucose concentration; FIG. 4 (B): areas under the curves (AUC) of oral glucose tolerance calibrated according to calibration group, *p<0.05, *p<0.001, as compared with control group; FIG. 4 (C): concentrations of serum insulin at 20 minutes after oral administration of glucose, p<0.01 as compared with control group.

Figure 5:
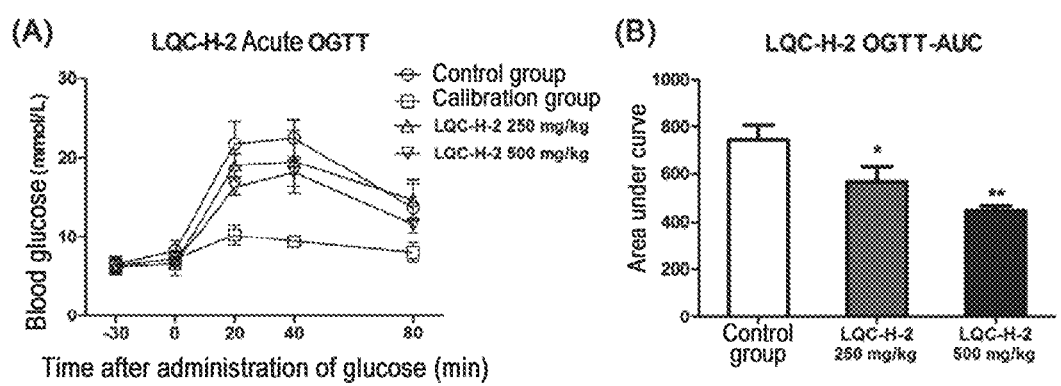

FIG. 5 shows that the extracts of *Glechoma longituba* (Nakai) Kupr., LQC-H-2, at both 250 mg/kg and 500 mg/kg could significantly enhance acute oral glucose tolerance in mice. Note: FIG. 5 (A): LQC-H-2 enhanced acute oral glucose tolerance in mice, where the abscissa is time after administration of glucose and the ordinate is blood glucose concentration; FIG. 5 (B): areas under the curves (AUC) of oral glucose tolerance calibrated according to calibration group, *p<0.05, **p<0.01, as compared with control group.

Figure 6:
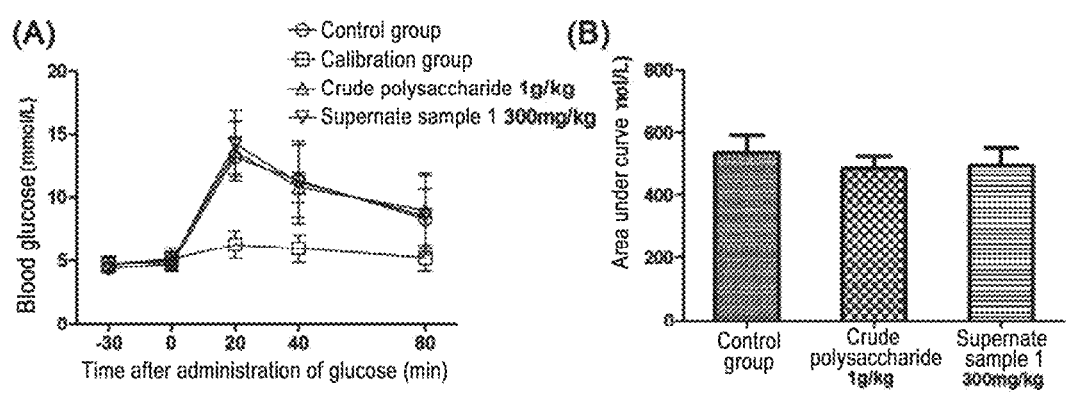

FIG. 6 shows that none of the supernate of the extract of *Glechoma longituba* (Nakai) Kupr. by extraction with water and precipitation with alcohol and the crude polysaccharide in the alcohol precipitated solid enhances acute oral glucose tolerance in mice. Note: FIG. 6 (A): none of the crude polysaccharide and the supernate component by extraction with water and precipitation with alcohol of *Glechoma longituba* (Nakai) Kupr. enhances acute oral glucose tolerance in mice, where the abscissa is time after administration of glucose and the ordinate is blood glucose concentration; FIG. 6 (B): areas under the curves of oral glucose tolerance calibrated according to calibration group, where the difference between the administration group and control group had no statistical significance.

Figure 7:
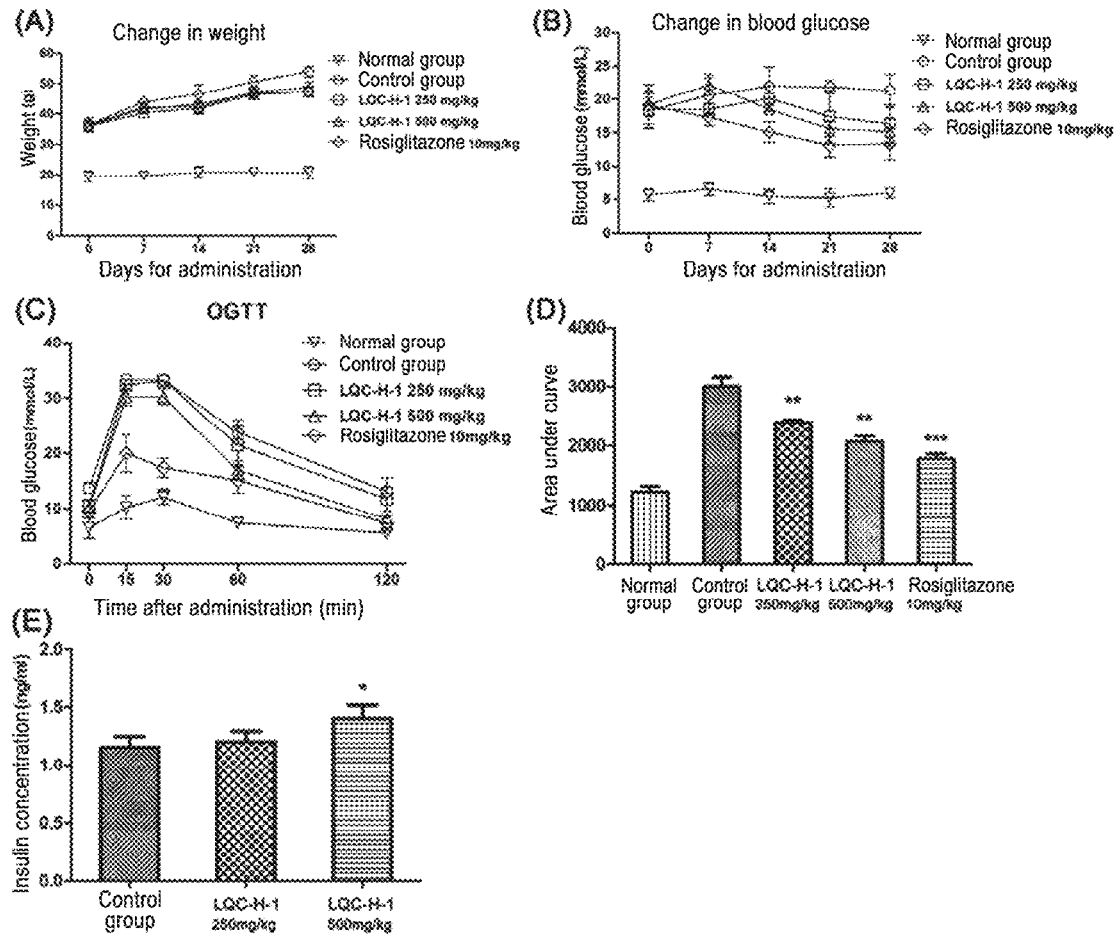

FIG. 7 shows that long term administration of the extract of *Glechoma longituba* (Nakai) Kupr., LQC-H-1, improved diabetic symptom of spontaneous diabetes mellitus type 2 model db/db mice. Note: FIG. 7 (A): LQC-H-1 did not significantly affect the weight of mice, while long term administration of rosiglitazone increased the weight of mice, where the abscissa is administration time and the ordinate is weight; FIG. 7 (B): LQC-H-1 lowered instant blood glucose in db/db mice, the effect of which was similar to the positive drug, rosiglitazone, where the abscissa is administration time and the ordinate is blood glucose, #p<0.05 by the comparison of 250 mg/kg dosage group and control group, *p<0.05 by the comparison of 500 mg/kg dosage group and control group; FIG. 7 (C): LQC-H-1 enhanced acute oral glucose tolerance in mice at 4 weeks after administration, of which the effect was similar to the positive drug, rosiglitazone, where the abscissa is time after administration of glucose and the ordinate is blood glucose concentration; FIG. 7 (D): area under the curve of each group, p<0.01, *p<0.001, as compared with control group; FIG. 7 (E): LQC-H-1 increased serum insulin level of db/db mouse at 4 weeks after administration, *p<0.05, as compared with control group.

Figure 8:
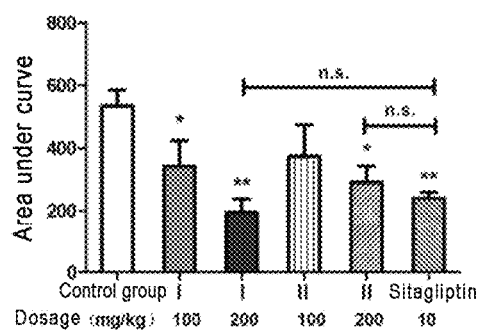
Figure 8:
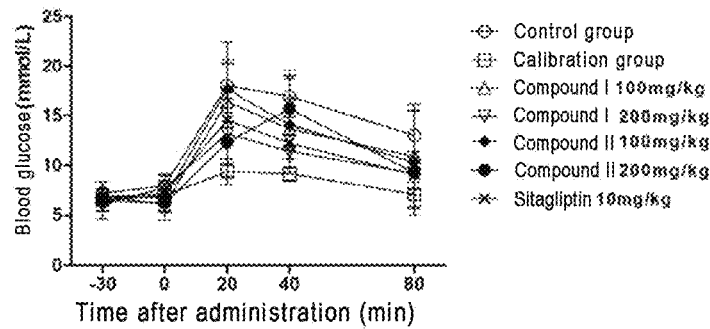

FIG. 8 shows that the primary active individual Compound I and Compound II in the extract of *Glechoma longituba* (Nakai) Kupr., as effective DPP4 inhibitors derived from natural products, could act alone to significantly enhance acute oral glucose tolerance in mice. Note: FIG. 8 (A): in vitro inhibitory activities of Compound I and Compound II against DDP4 enzyme, with Sitagliptin as positive control; FIG. 8 (B): Compound I and Compound II enhanced acute oral glucose tolerance in mice, with Sitagliptin as positive control, where the abscissa is time after administration of glucose and the ordinate is blood glucose concentration; Figure (C): areas under the curves (AUC) of oral glucose tolerance calibrated according to calibration group, *p<0.05, **p<0.01, as compared with control group; n.s. refers to that the differences of dosage groups of compounds at 200 mg/kg and Sitagliptin at 10 mg/kg had no statistical significance.

Figure 9:
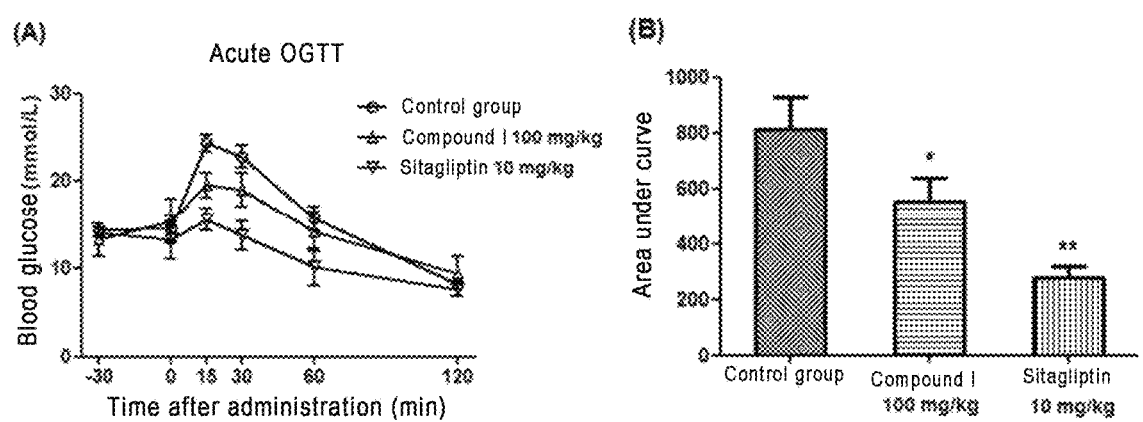

FIG. 9 shows that the primary active individual Compound I in the extract of *Glechoma longituba* (Nakai) Kupr. at the dosage of 100 mg/kg could significantly enhances acute oral glucose tolerance in mice. Note: FIG. 9 (A): acute oral glucose tolerance test in mice, where the abscissa is time after administration of glucose and the ordinate is blood glucose concentration; FIG. 9 (B): area under the curve of oral glucose tolerance of each group of mice, *p<0.05, **p<0.01, as compared with control group.

Figure 10:
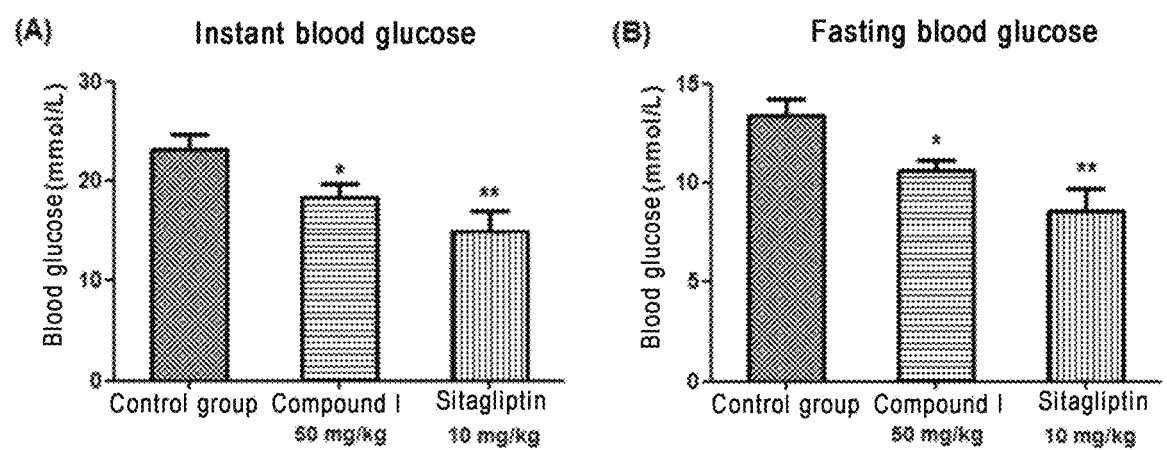

FIG. 10 shows that long term administration of Compound I could effectively lower blood glucose of db/db mice. Note: FIG. 10 (A): Compound I lowered instant blood glucose of mice at 2 weeks after administration, the effect of which was close to the positive drug, Sitagliptin; FIG. 10 (B): Compound I lowered fasting blood glucose of mice at 2 weeks after administration, the effect of which was close to the positive drug, Sitagliptin, *p<0.05, **p<0.01, as compared with control group.

Figure 11:
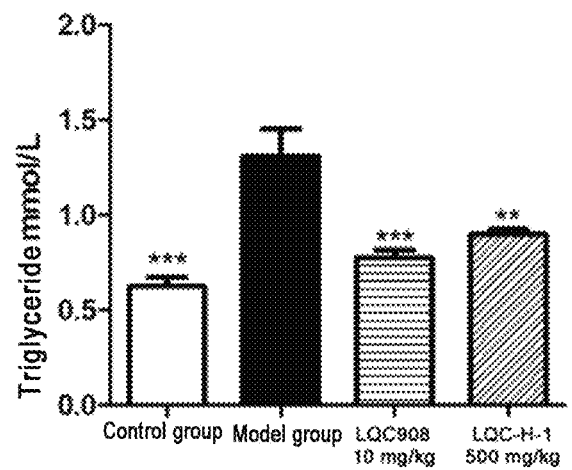

FIG. 11 shows that the extract of *Glechoma longituba* (Nakai) Kupr., LQC-H-1, could lower serum triglyceride level in acute hypertriglyceridemic mice. Note: the extract of *Glechoma longituba* (Nakai) Kupr., LQC-H-1, could lower serum triglyceride level in acute hypertriglyceridemic mice, with LCQ908 at 10 mg/kg as positive control; the model group was modeled by administrating 2 g/kg olive oil, while the blank group was modeled by not administrating olive oil. p<0.01, *p<0.001.

Figure 12:
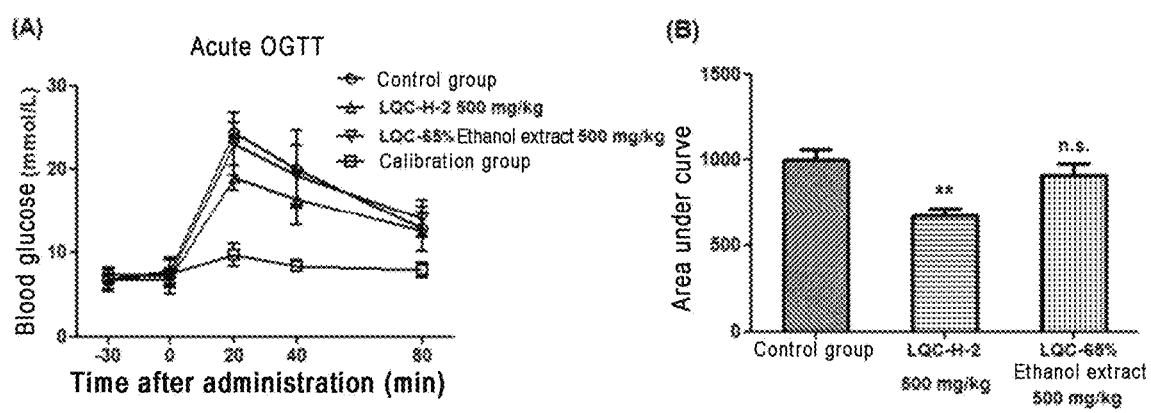

FIG. 12 shows that 65% ethanol ultrasonic extract of *Glechoma longituba* (Nakai) Kupr. (LQC-65% ethanol extract) did not significantly affect acute glucose tolerance in mice. Note: FIG. 12(A): acute oral glucose tolerance test in mice, where the abscissa is time after administration of glucose and the ordinate is blood glucose concentration; FIG. 12 (B): areas under the curves of oral glucose tolerance calibrated according to calibration group, **p<0.01, n.s.=no significant difference.

DETAILED DESCRIPTION

Materials, Reagents, and Equipment

*Glechoma longituba* (Nakai) Kupr. material: bought from Shanghai Kangqiao traditional Chinese medicine decoction pieces limited company on August 2012; lot number: 120713; production date: Jul. 16, 2012.

Reagents: the reagent of 95% ethanol, distilled water, ethyl acetate, dichloromethane, methanol, etc. are all analytical grade (Sinopharm Chemical Reagent Co., Ltd); D101 macroporous adsorption resin (Sinopharm Chemical Reagent Co., Ltd.), column chromatography silica gel (H series, Qingdao Ocean Silica Gel Desiccant Factory), thin layer chromatography silica gel GF254 (Qingdao Ocean Silica Gel Desiccant Factory), MCI chromatography filler (Japan, GEL CHP20P, 75-100μ), ODS chromatography filler (Japan, YMC*GEL, s 50 μm), Sephadex LH-20 chromatography filler (Sweden, GE Healthcare).

Equipment:

Rotary evaporator: EYELA Rotary evaporator N1001, EYELA.

Lyophilizer: Christ, ALPHA 1-2LD PLUS, Germany.

Electronic balance, BT 125D, Sartorius Scientific Equipment (Beijing) Co., Ltd. Camera obscura UV transilluminator: WFH-203B, Shanghai Jingke Industrial Co., Ltd.

Ultrasonic equipment: SK7200H (350 W), Shanghai Kedao Ultrasonic Equipment Co., Ltd.

ESI-MS: determined with Finnigan LCQ-DECA mass spectrometer.

NMR: determined with Varian INOVA 400 nuclear magnetic resonance spectrometer, with TMS as internal reference.

High performance liquid chromatography (HPLC): Agilent 1260 high performance liquid system, DAD detector.

Example 1

The Preparation of the Extract of *Glechoma longituba* (Nakai) Kupr

The present example provides three methods for preparing the extract of whole plant of *Glechoma longituba* (Nakai) Kupr.

(1) To 100 g of the whole plant of traditional Chinese medicine, *Glechoma longituba* (Nakai) Kupr., water was added twice for reflux extraction. The amount of water added for the first time was 15 times of the weight of the medicinal material, which was subjected to heating reflux for 1.5 h at 100° C. after being immersed for 15 mins. The amount of water added for the second time was 10 times of the weight of the medicinal material, which was subjected to heating reflux for 1.5 h at 100° C. The extract liquids are combined after filtration. The combined extract liquid was concentrated to 400 ml under reduced pressure at 50-55° C. using the rotary evaporator, followed by five times extraction with equal-volume ethyl acetate. The extract liquids in ethyl acetate layers were combined. The remaining aqueous layers were concentrated to 190 ml under reduced pressure and refrigerated for 3-4 h at 4° C. in a refrigerator. Then, it was took out, added with 95% (v/v) ethanol solution in an amount of three times, sufficiently stirred, refrigerated for 12 h at 4° C. in a refrigerator, and filtrated. The filtrate and the extract liquid of ethyl acetate were combined and concentrated under reduced pressure to obtain supernate sample 1. The residual ethanol solution was removed from the alcohol precipitated solid in environment at 50° C. using a drying oven under reduced pressure to obtain an alcohol precipitated extract, which was froze for 12 h in –70° C. freezer and then lyophilized for 48 h using the lyophilizing equipment (Christ lyophilizer) to obtain 21.04 g dry solid powder of the extract of *Glechoma longituba* (Nakai) Kupr. (LQC-H-1).

(2) To 100 g of the whole plant of traditional Chinese medicine, *Glechoma longituba* (Nakai) Kupr., water was added twice for reflux extraction. The amount of water added for the first time was 15 times of the weight of the medicinal material, which was subjected to heating reflux for 1.5 h at 100° C. after being immersed for 15 mins. The amount of water added for the second time was 10 times of the weight of the medicinal material, which was subjected to heating reflux for 1.5 h at 100° C. The extract liquids were combined after filtration, concentrated to 200 ml under reduced pressure at 50-55° C. using the rotary evaporator, and refrigerated for 3-4 h at 4° C. in a refrigerator. Then, it was took out, added with 95% (v/v) ethanol solution in an amount of three times, sufficiently stirred, refrigerated for 12 h at 4° C. in a refrigerator, and filtrated. The supernate was concentrated under reduced pressure at 50° C. using the rotary evaporator to obtain supernate sample 2. The residual ethanol solution was removed from the alcohol precipitated solid in environment at 50° C. using a drying oven under reduced pressure. The resulting was froze for 12 h in –70° C. freezer and then lyophilized for 48 h using the lyophilizing equipment (Christ lyophilizer) to obtain 19.2 g dry solid powder of the extract of *Glechoma longituba* (Nakai) Kupr. (LQC-H-2).

(3) To 100 g of the whole plant of traditional Chinese medicine, *Glechoma longituba* (Nakai) Kupr., water was added twice for ultrasonic extraction. The amount of water added for the first time was 15 times of the weight of the medicinal material, which was subjected to ultrasonic extraction for 45 mins after being immersed for 15 mins. The extract liquid was collected by filtration. The amount of water added for the second time was 10 times of the weight of the medicinal material, which was subjected to ultrasonic extraction for 45 mins. The two extract liquids were combined after filtration, concentrated to 200 ml under reduced pressure at 50-55° C. using the rotary evaporator, and refrigerated for 3-4 h at 4° C. in a refrigerator. Then, it was took out, added with 95% (v/v) ethanol solution in an amount of three times, sufficiently stirred, refrigerated for 12 h at 4° C. in a refrigerator, and filtrated. The supernate was concentrated under reduced pressure at 50° C. using the rotary evaporator to obtain supernate sample 3. The residual ethanol solution was removed from the alcohol precipitated solid in environment at 50° C. using a drying oven under reduced pressure. The resulting was froze for 12 h in –70° C. freezer and then lyophilized for 48 h using the lyophilizing equipment (Christ lyophilizer) to obtain 14.1 g dry solid powder of the extract of *Glechoma longituba* (Nakai) Kupr. (LQC-H-3).

Example 2: Separation and Identification of Primary Ingredients in the Supernate after Precipitation with Alcohol in the Process for Preparing the Extract of *Glechoma longituba* (Nakai) Kupr 200 mg concentrated extract of supernate sample 1 in Example 1 was dissolved by the addition of a small amount of distilled water, separated and purified with MCI filler, gradient eluted with methanol-water (water, 20% methanol, 40% methanol, 60% methanol, 100% methanol), and analyzed by HPLC. Elution fractions of 40% methanol and 60% methanol were selected for subsequent separation. 40% elution fraction was concentrated to an extract under reduced pressure at 50° C. using the rotary evaporator, dissolved with a small amount of methanol, separated and purified with ODS filler, and isocratic eluted with 30% methanol. Main peak 1 (t=13.04 min, 5.4 mg) was obtained after purification. 60% elution fraction was concentrated to an extract under reduced pressure at 50° C. using the rotary evaporator, dissolved with a small amount of methanol, separated and purified with ODS filler, and isocratic eluted with 40% methanol. The eluate was concentrated under reduced pressure and isocratic eluted with 20% methanol on Sephadex LH-20 filler. Main peak 2 (t=29.98 min, 2.4 mg) was obtained after purification.

Main peak 1 (t=13.04 min) in supernate sample 1 was yellow amorphous powder (methanol). After determination by ESI-MS, anion m/z: 179 [M–H]⁻; 1H NMR (CD3OD, 400 MHz) δ: 7.35 (1H, d, J=15.8 Hz, H-7), 7.01 (1H, d, J=2.0 Hz, H-2), 6.88 (1H, dd, J=8.1, 2.0 Hz, H-6), 6.75 (1H, d, J=8.1 Hz, H-5), 6.29 (1H, d, J=15.8 Hz, H-8), which was consistent with that reported by the reference (Wang M F, et al. J Agric Food Chem, 2000, 48: 235-238.), was identified as caffeic acid.

After determination by ESI-MS, main peak 2 (t=29.98 min), anion m/z: 359 [M–H]⁻, 719 [2M–H]–; 1H NMR (CD3OD, 400 MHz) δ: 7.53 (1H, d, J=15.8 Hz, H-7), 7.05 (1H, d, J=1.9 Hz, H-2), 6.94 (1H, dd, J=8.2, 1.9 Hz, H-6), 6.79 (1H, d, J=8.2 Hz, H-5), 6.78 (1H, d, J=1.8 Hz, H-2'), 6.69 (1H, d, J=8.0 Hz, H-5'), 6.65 (1H, dd, J=8.0, 1.8 Hz, H-6'), 6.28 (1H, d, J=15.8 Hz, H-8), 5.11 (1H, d, J=9.3 Hz, H-8'), 3.13 (1H, d, J=13.6 Hz, H-7'(a)), 2.97 (1H, d, J=13.6, 9.3 Hz, H-7'(β)); 13C NMR (CD3OD, 100 MHz) δ: 173.7 (C-9'), 167.7 (C-9), 148.2 (C-4), 145.5 (C-7), 145.4 (C-3), 144.6 (C-3'), 143.5 (C-4'), 129.5 (C-1'), 126.4 (C-1), 121.6 (C-6), 120.3 (C-6'), 116.1 (C-2'), 115.1 (C-5), 114.8 (C-5'), 114.0 (C-8), 113.6 (C-2), which was consistent with that reported by the reference (Ha T J, et al. Food Chemistry, 2012, 135: 1397-1403.), was identified as rosmarinic acid.

Example 3: Analysis and Detection of Primary Ingredients in the Extract of *Glechoma longituba* (Nakai) Kupr. Using HPLC The primary ingredients in the extracts of *Glechoma longituba* (Nakai) Kupr., LQC-H-1, LQC-H-2, LQC-H-3, and supernate sample 1, sample 2, and sample 3 were compared for analysis using HPLC, and the contents of Compound I and Compound II in the extracts were determined. The results were shown in FIG. 1. The chromatography conditions were as follows:

Model of chromatographic column: Agilent ZORBAX SB-C18, 5 μm, 4.6×250 mm Mobile phase: acetonitrile (A)—water (B, containing 0.2% acetic acid); flow rate: 1 ml/min Sample concentrations: LQC-H-1(21 mg/ml), LQC-H-2 (24 mg/me, LQC-H-3(20 mg/ml), supernate sample 1(7.16 mg/me, sample 2(7.20 mg/ml), sample 3(6.8 mg/ml)

The control groups as obtained by the method according to the prior art (Yuan Chunlin, et al., *Pharmacology and Clinics of Chinese Materia Medica*, 2008, 24(3), 57-58; Yang Nianyun, et al., *Journal of China Pharmaceutical University*, 2005, 36(3), 210-212): 65% ethanol ultrasonic extract (16.2 mg/ml), 80% ethanol reflux extract (16.5 mg/ml). The results of primary ingredient detection were shown as FIG. 2.

Injection volume: 10 μl

Detection wavelength: 190-400 nm, preferably 360 nm for content determination Conditions for gradient elution were shown in Table 1:

TABLE 1

Conditions for HPLC gradient elution

| | Mobile phase | |
|---|---|---|
| Time | Acetonitrile (A) | Water (B, containing 0.2% acetic acid) |
| 0 | 10 | 90 |
| 3 | 10 | 90 |
| 11 | 14 | 86 |
| 15 | 16 | 84 |
| 20 | 18 | 82 |

TABLE 1-continued

Conditions for HPLC gradient elution

| | Mobile phase | |
|---|---|---|
| Time | Acetonitrile (A) | Water (B, containing 0.2% acetic acid) |
| 35 | 25 | 75 |
| 42 | 30 | 70 |
| 50 | 50 | 50 |
| 65 | 80 | 20 |
| 70 | 95 | 5 |

Figure 1:
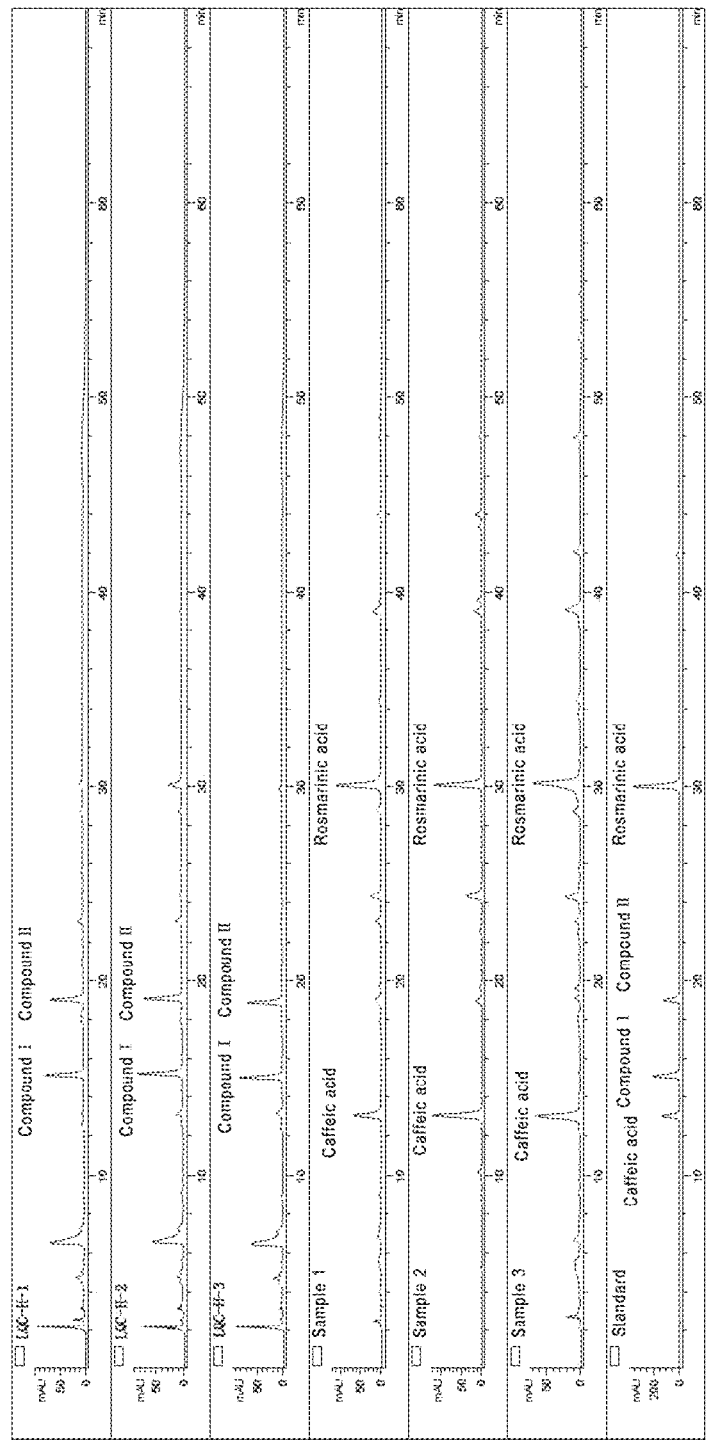
FIG. 1 shows the HPLC analysis results of primary ingredients of the extract of *Glechoma longituba* (Nakai) Kupr. obtained by various preparation processes.

The analysis result in FIG. 1 showed that the main peaks of LQC-H-1, LQC-H-2, and LQC-H-3, extracts of *Glechoma longituba* (Nakai) Kupr. prepared by three processes, had consistent heights. It indicated that all of the three processes of the present invention could effectively obtain active Compound I and Compound II. The process for LQC-H-2 omitted the extraction process with ethyl acetate reagent and had a high yield. In view of manufacture, it was quicker, safer, and more cost-saving, and was a preferred process of preparing the extract of *Glechoma longituba* (Nakai) Kupr. In addition, the primary ingredients in supernate sample 1, sample 2, and sample 3 produced by three processes were highly consistent, which were caffeic acid and rosmarinic acid. This demonstrated that the direct use of the process of extraction with water and precipitation with alcohol could achieve the same effect of ethyl acetate extraction.

In addition, the analysis results in FIG. 1 showed that flavone compounds were effectively obtained by collecting solid precipitate using the process of extraction with water and precipitation with alcohol. The precipitate well enriched Compound I and Compound II, from which caffeic acid compounds were quickly removed. By determination using external reference method, the percentages of Compound I and Compound II in the three extracts were: Compound I accounted for 0.87% and Compound II accounted for 0.81% in LQC-H-1; Compound I accounted for 0.79% and Compound II accounted for 0.75% in LQC-H-2; Compound I accounted for 0.50% and Compound II accounted for 0.59% in LQC-H-3, respectively. Both contents of caffeic acid and rosmarinic acid in the solid were less than 0.1%.

Figure 2:
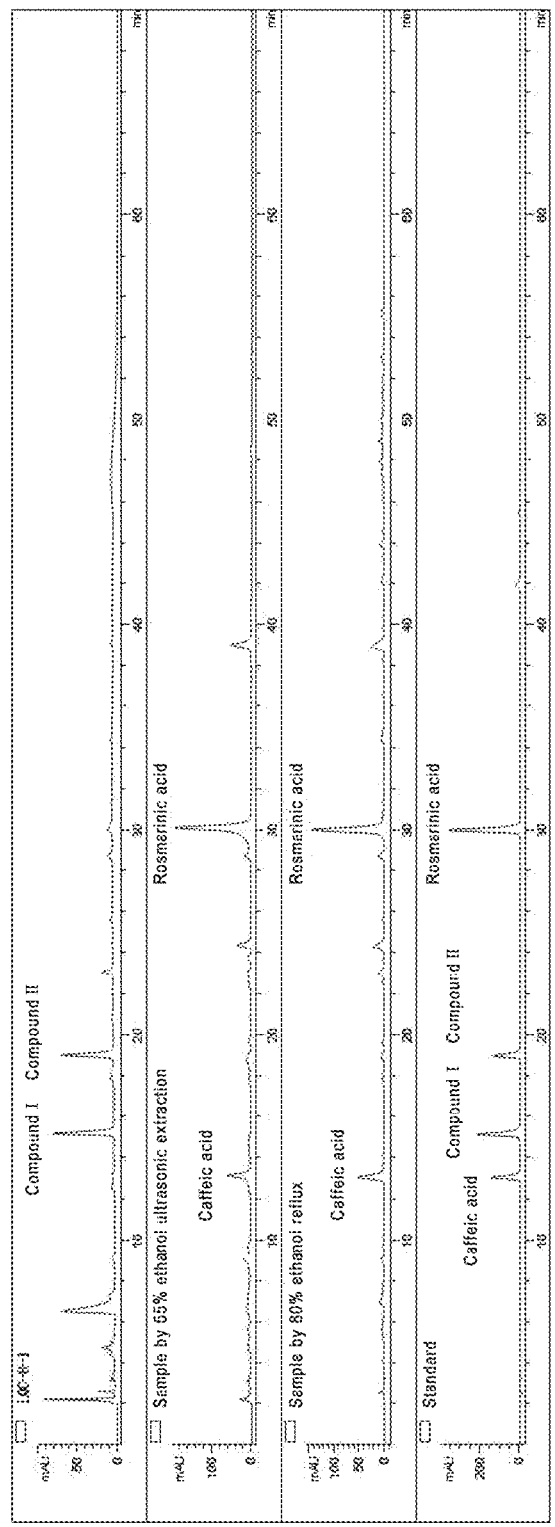
FIG. 2 shows the HPLC analysis results of primary ingredients in the extract of *Glechoma longituba* (Nakai)

The analysis results in FIG. 2 showed that under the same test conditions as the present invention, the extracts obtained by the extraction methods recited in prior art (Yuan Chunlin, et al., *Pharmacology and Clinics of Chinese Materia Medica*, 2008, 24(3), 57-58; Yang Nianyun, et al., *Journal of China Pharmaceutical University*, 2005, 36(3), 210-212) did not show any obvious HPLC absorption peak of Compound I and Compound II, indicating that the methods reported in prior art references failed to effectively obtain Compound I and Compound II.

Example 4: The Preferred Preparation Process and Structure Analysis of Primary Active Ingredients, Compound I and Compound II, in the Extracts of *Glechoma Longituba* (Nakai) Kupr To 200 g of the whole plant (had already been cut and smashed) of traditional Chinese medicine, *Glechoma longituba* (Nakai) Kupr., water was added twice for reflux extraction. The amount of water added for the first time was 15 times of the weight of the medicinal material, which was subjected to heating reflux for 1.5 h at 100° C. after being immersed for 15 mins. The amount of water added for the second time was 10 times of the weight of the medicinal material, which was subjected to heating reflux for 1.5 h at 100° C. The extract liquids were combined after filtration, concentrated to 380 ml under reduced pressure at 50-55° C. using the rotary evaporator, and refrigerated for 3-4 h at 4° C. in a refrigerator. Then, it was took out, added with 95% (v/v) ethanol solution in an amount of three times, sufficiently stirred, and refrigerated for 12 h at 4° C. in a refrigerator. After filtration, an alcohol precipitated solid was collected. After sufficient dissolution of the alcohol precipitated solid by the addition of water, residual ethanol solution was removed by concentration under reduced pressure at 50° C. using the rotary evaporator to obtain 400 ml concentration liquid of the aqueous layer. It was separated using 1 kg D101 macroporous adsorption resin, followed by elution of protein and polysaccharide components with 2400 ml distilled water and subsequent elution with 2000 ml 15% ethanol, and then the eluate was collected. The eluate was concentrated under reduced pressure at 50-55° C. using the rotary evaporator to obtain an extract enriched in Compound I and Compound II. The method for content determination was consistent with that in Example 3. The contents of Compound I and Compound II were 13.78% and 12.77%, respectively, the sum of which accounted for 26.55% of the weight of the extract. The contents of caffeic acid and rosmarinic acid were less than 0.01% (see FIG. 3).

The aforementioned extract (Compounds I and II accounted for 26.55% of the overall extract) could be separated again using 300 g D101 macroporous adsorption resin, followed by elution of residual protein and polysaccharide components with 400 ml distilled water and subsequent elution with 800 ml distilled water, and then the eluate was collected. The eluate was concentrated under reduced pressure at 50-55° C. using the rotary evaporator to obtain an extract enriched in Compound I and Compound II. The contents of Compound I and Compound II were 29.70% and 26.91%, respectively, the sum of which accounted for 56.61% of the weight of the extract (see FIG. 3).

The aforementioned extract (Compounds I and II accounted for 56.61% of the overall extract) could be sequentially separated using 200 g D101 macroporous adsorption resin for the third separation and purification, followed by elution of pigment with 200 ml distilled water and subsequent elution with 500 ml distilled water, and then the eluate was collected. The eluate was concentrated under reduced pressure at 50-55° C. using the rotary evaporator to obtain an extract enriched in Compound I and Compound II. The contents of Compound I and Compound II were 39.75% and 32.77%, respectively, the sum of which accounted for 72.52% of the weight of the extract (see FIG. 3).

All the above three extracts comprising Compound I and Compound II in different ratios purified with macroporous resin could be dissolved with a small amount of distilled water, quickly purified with YMC*GEL ODS filler, and each gradient eluted with water and 10% methanol. The collected fractions were analyzed by HPLC. The same components were combined and then concentrated under reduced pressure at 50° C. with the rotary evaporator to obtain totally 296 mg of individual Compound I (purity of 98.65%, see FIG. 3) and totally 258 mg of individual Compound II (purity of more than 96.52%, see FIG. 3).

Compound I was brown amorphous powder (methanol). Anion ESI-MS m/z: 637 [M−H]$^-$; cation ESI-MS m/z: 639 [M+H]+. 1H NMR (DMSO-d6+D20, 400 MHz) δ: 7.47 (2H, d, J=1.9 Hz, H-2'), 7.43 (1H, dd, J=8.2, 1.9 Hz, H-6'), 6.96 (1H, s, H-3), 6.89 (1H, d, J=8.2 Hz, H-5'), 6.71 (1H, d, J=2.2 Hz, H-8), 6.49 (1H, d, J=2.2 Hz, H-6), 5.20 (1H, d, J=6.5 Hz, H-1''), 4.57 (1H, d, J=6.3 Hz, H-1'''), 3.20-4.1 (m, hidden). 13C NMR (DMSO-d6+D20, 100 MHz) δ: 182.4 (C-4), 172.9 (C-6'''), 170.2 (C-6''), 164.9 (C-2), 163.2 (C-7), 161.0 (C-9), 157.2 (C-5), 150.1 (C-4'), 146.0 (C-3'), 121.7 (C-1'), 119.6 (C-6'), 116.5 (C-5'), 113.7 (C-2'), 105.8 (C-1''), 104.0 (C-10), 103.4 (C-3), 100.3 (C-6), 98.5 (C-1'''), 96.2 (C-8), 81.8 (C-2''), 76.2 (C-5'''), 75.8 (C-3''), 75.1 (C-5''), 74.6 (C-3'''), 74.4 (C-2'''), 72.2 (C-4''), 71.6 (C-4'''). The above data was consistent with the data reported in the reference (Berashili D T, et al. Chemistry of Natural Compound, 2006, 42(1): 106-107). For the first time, the present invention separated Compound I from *Glechoma* Linn. plants.

Compound I was brown amorphous powder (methanol). Anion ESI-MS m/z: 621 [M−H]$^-$; cation ESI-MS m/z: 645 [M+Na]$^+$. 1H NMR (DMSO-d6+D20, 400 MHz) δ: 7.95 (2H, d, J=8.0 Hz, H-2',6'), 6.94 (2H, d, J=8.0 Hz, H-3',5'), 6.93 (1H, hidden, H-3), 6.80 (1H, d, J=1.9 Hz, H-8), 6.52 (1H, d, J=1.9 Hz, H-6), 5.21 (1H, d, J=6.6 Hz, H-1''), 4.57 (1H, d, J=6.4 Hz, H-1'''), 3.20-4.10 (m, hidden). 13C NMR (DMSO-d6+D20, 100 MHz) δ: 182.5 (C-4), 172.7 (C-6'''), 171.8 (C-6''), 164.8 (C-2), 163.2 (C-7), 161.6 (C-9), 161.1 (C-4'), 157.3 (C-5), 129.2 (C-2',6'), 121.4 (C-1'), 116.5 (C-3',5'), 105.8 (C-10), 103.7 (C-1'''), 103.4 (C-3), 100.3 (C-6), 98.3 (C-1''), 96.0 (C-8), 81.5 (C-2''), 76.4 (C-5'''), 75.9 (C-3''), 75.1 (C-5''), 74.9 (C-3'''), 74.4 (C-2'''), 72.2 (C-4''), 71.8 (C-4'''). The above data was consistent with the data reported in the reference (Chen Zenai, et al., *Acta Pharmaceutica Sinica*, 1988, 23(10): 789-791).

Example 5: The Extract of *Glechoma longituba* (Nakai) Kupr., LQC-H-1, Significantly Enhanced Acute Oral Glucose Tolerance in Mice and Increased Blood Insulin Level in Mice after Oral Administration of Glucose Oral glucose tolerance test (OGTT) method: 8-week old male C57BL/KsJ mice (Shanghai Slac Laboratory Animal Company), 8 for each group, weight of 20±2 g, were fed according to SPF grade operation procedure and fasted for 16 hours prior to experiment. Blood was collected from tail vein of each group of mice prior to experiment. Blood glucose concentrations were measured using Roche ACCU-CHEK glucometer and recorded as time 0. Different concentrations of the compound were intragastric administrated to each administration group of mice, respectively. Equal volume of distilled water was given to control group of mice. The dosage volume was 10 ml/kg. Half an hour after administration, 5 g/kg glucose was intragastric administrated to each group of mice. Blood glucose concentrations of each group of mice were measured and recorded at 20 mins, 40 mins, and 80 mins after the intragastric administration. OGTT curves were recorded. Areas under the curves (AUC) were calibrated with the data in blood glucose of mice to which glucose was not given (calibration group). ONE-WAY-ANOVA was used to compare significant difference between each group (Note: all the experimental methods for acute oral glucose tolerance test in the following activity examples are the same to the experimental method in Example 5, unless otherwise indicated). Blood was collected from tail vein at 20 mins after oral administration of glucose for mice. ELISA (kit was bought from Millipore, USA) was utilized for measuring blood insulin level of mice.

Animal grouping: control group; calibration group; LQC-H-1 lower dose group (250 mg/kg); LQC-H-1 higher dose group (500 mg/kg).

Experimental results: the extracts of *Glechoma longituba* (Nakai) Kupr., LQC-H-1, at both 250 mg/kg and 500 mg/kg could significantly enhance acute oral glucose tolerance in mice and increase blood insulin level in mice after oral administration of glucose (FIG. 4). This effect was concentration-dependent, suggesting that this extract acted to promote secretion of insulin from pancreatic islet β-cells and to improve postprandial blood glucose.

Example 6: The Extract of *Glechoma longituba* (Nakai) Kupr., LQC-H-2, Also could Significantly Enhance Acute Oral Glucose Tolerance in Mice The experimental method was the same to Example 5. Animal grouping: control group; calibration group; LQC-H-2 lower dose group (250 mg/kg); LQC-H-2 higher dose group (500 mg/kg).

Experimental results: the extracts of *Glechoma longituba* (Nakai) Kupr., LQC-H-2, at both 250 mg/kg and 500 mg/kg could significantly enhance acute oral glucose tolerance in mice (FIG. 5).

Example 7: None of the Supernate of the Extract of *Glechoma longituba* (Nakai) Kupr. By Extraction with Water and Precipitation with Alcohol and the Crude Polysaccharide in the Alcohol Precipitated Solid Enhanced Acute Oral Glucose Tolerance in Mice The experimental method was the same to Example 5. Animal grouping: control group; crude polysaccharide group (1 g/kg); post-alcohol precipitation supernate sample 1 group (300 mg/kg).

The above activity tests demonstrated that the supernate of the extract of *Glechoma longituba* (Nakai) Kupr. by extraction with water and precipitation with alcohol and the alcohol-precipitated crude polysaccharide component were not active parts for glucose decrease (FIG. 6). The application of process in Example 1 could effectively remove caffeic acid components without blood glucose decreasing activity from the extract of *Glechoma longituba* (Nakai) Kupr., thereby improving the blood glucose decreasing effect of the extract. Meanwhile, it is demonstrated that the presumption of the reference (Shinji I., et al. Nippon Shokuhin Kagaku Kogaku Kaishi, 2007, 54(9):412-414) that water soluble dietary fibers (most of them are polysaccharide ingredients) are effective blood glucose decreasing components is incorrect. The parts playing blood glucose decreasing activity in the water soluble components should be attributed to Compound I, Compound II, or a mixture thereof.

Example 8: Long Term Administration of the Extract of *Glechoma longituba* (Nakai) Kupr, LQC-H-1, Improved Diabetic Symptom of Spontaneous Diabetes Mellitus Type 2 Model Db/Db Mice Experimental method: 8-week old male db/db spontaneous obesity diabetes mellitus type 2 model mice (background: C57BL/KsJ, Jackson Lab, USA), 8 for each group, initial weight of 30±2 g, were fed according to SPF grade operation procedure. The mice were divided into 3 groups: equal volume of distilled water was given to control group of mice; lower dose group (250 mg/kg) and higher dose group (500 mg/kg) were intragastric administrated with LQC-H-1, respectively; insulin sensitizer, rosiglitazone (10 mg/kg), was used as positive drug and administrated simultaneously; mice of the same variety that are normal in blood glucose (db/m) were used as blank for comparison. Dosage volume was 10 ml/kg, once a day for 4 weeks. Weight, blood glucose, and dietary change of the mice were monitored every week. 4 weeks later, OGTT of each group of mice was determined according to the method in Example 1 without acute administration of medicament, and AUC was calculated. Serum was collected to measure insulin content in mice. The improvement of diabetic symptom of spontaneous diabetes mellitus type 2 model db/db mice by long term administration of LQC-H-1 was evaluated.

Experimental results: administration of positive control, rosiglitazone, for 4 weeks increased db/db mice's weight, which may associate with the increase in blood lipid due to the long term administration of that drug. The extract of *Glechoma longituba* (Nakai) Kupr., LQC-H-1, did not significantly affect db/db mice's weight and diet (FIG. 7A), indicating that LQC-H-1 did not have significant toxicity. Meanwhile, LQC-H-1 at 250 mg/kg and 500 mg/kg lowered instant blood glucose of db/db mice; such a blood glucose decreasing effect was close to rosiglitazone (FIG. 7B). 4 weeks after administration, the extract of *Glechoma longituba* (Nakai) Kupr., LQC-H-1, could significantly improve oral glucose tolerance in db/db mice, which was similar to the effect of the positive drug (FIGS. 7C and 7D). In addition, as can be seen from the comparison of db/db mice in LQC-H-1 administration group with control group, serum insulin levels increased (FIG. 7E), indicating that the long term administration of LQC-H-1 could increase insulin level in mice, lower blood glucose of db/db mice, and improve symptom of diabetes mellitus type 2.

In the present experiment, the diet and weight of the mice were not significantly affected by LQC-H-1 after long term administration, while rosiglitazone resulted in weight gain of mice. Accordingly, long term administration of rosiglitazone resulted in side effects such as abnormal blood lipid. Therefore, it could be indicated that the extract, LQC-H-1, could not only simultaneously achieve blood glucose decreasing and blood lipid decreasing effects but also has higher safety than the positive drug, rosiglitazone.

Example 9: The Primary Active Individual Compound I and Compound II in the Extract of *Glechoma longituba* (Nakai) Kupr., as Effective DPP4 Inhibitors Derived from Natural Products, could Act Alone to Significantly Enhance Acute Oral Glucose Tolerance in Mice Experimental method: (1) determination of inhibiting activity of Compound I and Compound II against DDP4 enzyme in vitro: cell lysis solution of human colon cancer cell line Caco-2 as DDP4 enzyme source (Thomas, L., et al, 2008, JPET). In a drug screening system of 96-well plate, 100 µL/well, the final concentration of H-Gly-Pro-AMC substrate (AnaSpec) was 244 µM, in which different concentrations of test compounds were added for incubation at 37° C. for 30 mins Fluorescence signals were detected at excitation wavelength 380 nm/emission wavelengths 460 nm Inhibition rates (%) on the enzyme of test samples against DDP4 were calculated according to fluorescence absorption value obtained by detection. The inhibition rate (%) is calculated according to the following formula:

Inhibition rate (%)=($RFU$ blank–$RFU$ compound)/ ($RFU$ blank–$RFU$ negative control)*100%

RFU compound, RFU blank, and RFU negative control represent the difference of fluorescence values at 30 mins and at 0 min from a compound well, a blank well, and a negative control well free of enzyme; (2) effect of Compound I and Compound II for acute glucose tolerance in mice: the OGTT experimental method was the same to Example 5, the mice were divided into control group; calibration group; Compound I lower dose group (100 mg/kg); Compound I higher dose group (200 mg/kg); Compound II lower dose group (100 mg/kg); Compound II higher dose group (200 mg/kg); and positive drug group (Sitagliptin 10 mg/kg, Merck Company, USA).

Experimental results: (1) both Compound I and Compound II had varying degrees of inhibitory activity against DDP4, and the inhibition rates of them at 100 μM against DDP4 were 40.82±3.26% and 34.09±3.91%, respectively (FIG. 8A), and for the first time, it was reported that these two compound had inhibitory activity against DDP4; (2) Compound I and Compound II at both 100 mg/kg and 200 mg/kg could significantly enhance acute oral glucose tolerance in mice (FIGS. 8B and 8C), wherein Compound I had better activity than Compound II. Compound I and Compound II at higher dose (200 mg/kg) had activity comparable to the commercial chemical drug, Sitagliptin, at working concentration (10 mg/kg) (FIGS. 8B and 8C), and the same could effectively act to lower glucose and to control postprandial blood glucose, and was one of primary blood glucose decreasing active ingredients in the extract of *Glechoma longituba* (Nakai) Kupr.

Example 10: The Primary Active Individual Compound I in the Extract of *Glechoma longituba* (Nakai) Kupr. Improved Blood Glucose Control in Spontaneous Diabetes Mellitus Type 2 Model Db/Db Mice Experimental method: 8-week old male db/db spontaneous obesity diabetes mellitus type 2 model mice (C57BL/KsJ, Jackson Lab, USA), 8 for each group, initial weight of 30±2 g, were fed according to SPF grade operation procedure. The effect of Compound I on acute glucose tolerance in db/db mice were tested according to the method in Example 1. Animal grouping: control group; Compound I group (100 mg/kg); positive drug Sitagliptin group (10 mg/kg).

Experimental results: the primary active individual Compound I in the extract of *Glechoma longituba* (Nakai) Kupr. at the dosage of 100 mg/kg could significantly enhance acute oral glucose tolerance in mice, the effect of which was similar to commercial chemical drug, Sitagliptin (FIG. 9), indicating that Compound I as a DDP4 inhibitor derived from natural products also could significantly enhance acute glucose tolerance in spontaneous diabetes mellitus type 2 model db/db mice and might be one of primary active ingredients in the extract of *Glechoma longituba* (Nakai) Kupr., LQC-H-1, functioning to lower glucose in db/db mice After the end of the acute experiment, each group of mice undergone long term administration experiment following the grouping in below: equal volume of distilled water was given to control group of mice; Compound I at the dosage of 50 mg/kg was given to administration group; DDP4 inhibitor, Sitagliptin, at 10 mg/kg was intragastric administrated to positive control group. Dosage volume was 10 ml/kg, once a day for 4 weeks. Weight, blood glucose, and dietary change of the mice were monitored every week. The improvement of diabetic symptom of spontaneous diabetes mellitus type 2 model db/db mice by long term administration of Compound I was evaluated.

Experimental results: Compound I did not significantly affect the weight and diet of the mice. Two weeks after the administration, both instant blood glucose and fasting blood glucose significantly decreased (FIG. 10). It suggested that long term administration of Compound I could effectively lower blood glucose of db/db mice and improved symptom of diabetes mellitus type 2.

Example 11: Acute Blood Lipid Decreasing Activity Test of the Extract of *Glechoma longituba* (Nakai) Kupr., LQC-H-1

Experimental method: (1) the effect of the extract of *Glechoma longituba* (Nakai) Kupr., LQC-H-1, on serum triglyceride level was evaluated in acute hypertriglyceridemic mouse model; 6-week old male C57BL/KsJ mice (Shanghai Slac Laboratory Animal Company), 8 for each group, weight of 20±2 g, were fed according to SPF grade operation procedure and fasted overnight for 16 hours prior to experiment. Compounds of different concentrations were intragastric administrated to each administration group of mice, respectively. Equal volume of water was given to control group and blank group of mice. 30 mins later, 2 g/kg olive oil was intragastric administrated to administration group and control group of mice, while equal volume of water was given to blank group of mice. 2 hours later, blood was collected from orbital vein of each group of mice for the separation of serum, and concentration of triglyceride in the serum was measured; (2) inhibitory activity of the individual compounds separated from the extract of *Glechoma longituba* (Nakai) Kupr., LQC-H-1, against diacylglycerol acyltransferase (DGAT): human derived DGAT1 obtained by expression and purification with insect cells were pre-incubated together with the compounds, substrate diacylglycerol was added to initiate the reaction in the presence of coenzyme A, fluorescence signal generated by the combination of produced sulfydryl and CPM was measured, and the inhibitory activity of the compound against DGAT was calculated according to the following formula:

$$\text{Inhibition rate \%} = (OD\text{ blank} - OD\text{ compound})/(OD\text{ blank} - OD\text{ negative control}) * 100\%$$

OD compound, OD blank, and OD negative control represented the fluorescence values from a compound well, a blank well, and a negative control well free of DGAT1 enzyme, and the concentrations of the compounds when the enzyme activity inhibition rate (%) reached 50% were set as $IC_{50}$ value; (3) inhibitory activity of the individual compounds separated from the extract of *Glechoma longituba* (Nakai) Kupr., LQC-H-1, against pancrelipase: substrate p-Nitrophenyl acetate (Sigma, USA) was formulated to 1.35 mM with phosphate buffer (25 mM, pH 6.8); porcine pancrelipase (Sigma) was formulated to 10 mg/ml with phosphate buffer; brominated eneyne compounds were formulated to solutions of different concentrations with phosphate buffer. Then, 50 μl of 1.35 mM p-Nitrophenyl acetate (Sigma, USA) solution and 10 μl of test compounds of different concentrations were sequentially added into a 96-well plate and pre-incubated at 37° C. for 5 mins. Finally, 50 μl of 10 mg/ml pancrelipase (EC 3.1.1.3, Sigma, USA) was added and mixed. The reaction proceeded at 37° C. for further 20 mins Absorbance of each well was measured at 492 nm. The inhibition rates (%) of the test samples against pancrelipase were calculated based on the absorbance at 492 nm. The concentrations of the compounds when then enzyme activity inhibition rate (%) reached 50% was set as $IC_{50}$ value. The inhibition rate (%) could be calculated according to the following formula:

Inhibition rate (%)=[(A−B)−(C−D)]/(A−B)×100

In the above formula, A, B, C, and D represented the absorbance of a blank well after the reaction, the absorbance of a blank well prior to the reaction, the absorbance of a sample well after the reaction, and the absorbance of a sample well prior to the reaction.

Experimental results: (1) the extract of *Glechoma longituba* (Nakai) Kupr., LQC-H-1, at dosage of 500 mg/kg could lower the serum triglyceride level in the acute hypertriglyceridemic mice, the decreasing effect of which was close to the DGAT inhibitor, the positive drug LCQ908 (FIG. 11); (2) among the individual compounds separated from the extract of *Glechoma longituba* (Nakai) Kupr., LQC-H-1, Compounds I and II had significant DGAT inhibitory activity (see Table 2). The experimental results suggested that the extract of *Glechoma longituba* (Nakai) Kupr., LQC-H-1, had significant effect on acutely decreasing serum triglyceride, and that the compound having inhibitory activity against DGAT1 and pancrelipase (see Table 3) may be the primary effective ingredients for the function of LQC-H-1.

TABLE 2 inhibitory activity of individual compounds against hDGAT1

| | | Inhibition rate (%) | |
|---|---|---|---|
| No. | Compound No. | (50 μM) | (10 μM) |
| 1 | Compound I | 42.23 | 12.94 |
| 2 | Compound II | 52.89 | 23.85 |
| 3 | Positive drug, DGAT inhibitor A 922500 | 97.51 | 83.36 |

TABLE 3 inhibitory activity of individual compounds against pancrelipase

| No. | Compound No. | Inhibition rate % (50 μM) | Inhibition rate % (10 μM) |
|---|---|---|---|
| 1 | Compound I | 41.94 | / |
| 2 | Compound II | 41.63 | / |
| 3 | Olistat | | 83.96 |

Example 12: Inhibitory Activity of Compounds I and II Against GOX

GOX is an oxidase with flavin adenine mononucleotide (FMN) as auxiliary group, which catalyzes the oxidation of glycollic acid to oxalic acid. Overexpression of GOX would promote the production of oxalate, thereby increasing risks of kidney calculi and nephritis.

Mechanism of experiment: enzyme coupling method utilizes peroxidase (POD) and substrates thereof to react with generated $H_2O_2$ to produce colored products so as to determine the catalytic reaction rate of glucose oxidase. POD catalyzes $H_2O_2$ to react with phenol and 4-amino antipyrine to produce brown-red quinone substances.

Experimental method: reagents were added according to the table below; the reaction was immediately initiated upon the final addition of substrate glycolic acid; the kinetic course of the reaction was detected by microplate reader; the enzyme activity was represented by $V_{max}$, maximum reaction velocity.

Overall system: 200 μL

TABLE 8 method for formulating the reagent and concentration

| Reagent | Final concentration | Note |
|---|---|---|
| 1. 4-amino antipyrine | 500 μM | glycolic acid was replaced with water in negative control wells |
| 2. horseradish peroxidase | 2.5 U/mL | |
| 3. phenol | 1 mM | |
| 4. FMN | 50 μM | |
| 5. enzyme solution | 50 μl/ml | |
| 6. Compound (I) | 20 μl | |
| 7. Compound (II) | 20 μl | |
| 8. glycolic acid | 4 mM | |

Experimental results: the maximum velocities and inhibition rates when Compounds I and II were under the concentration gradient below (100 μM~0.1 μM; 3× dilution) were measured, and the experimental results were shown below (Table 9):

TABLE 9 measurement results of inhibitory activity of Compound I and Compound II against glucose oxidase

| | Compound I | | Compound II | | Quercetin (positive drug) | |
|---|---|---|---|---|---|---|
| Concentration | $V_{max}$ | Inhibition rate | $V_{max}$ | Inhibition rate | $V_{max}$ | Inhibition rate |
| 100 μM | 29.34 ± 0.10 | 17.78 ± 0.29 | 29.13 ± 0.80 | 18.37 ± 2.23 | −1.40 ± 8.87 | 103.93 ± 24.85 |
| 30 μM | 34.04 ± 0.65 | 4.60 ± 1.82 | 33.88 ± 0.98 | 5.05 ± 2.76 | 16.54 ± 0.12 | 53.66 ± 0.34 |
| 10 μM | 35.08 ± 0.21 | 1.69 ± 0.58 | 35.63 ± 1.00 | 0.15 ± 2.81 | 26.55 ± 0.15 | 25.59 ± 0.41 |
| 3 μM | 35.39 ± 0.63 | 0.83 ± 1.77 | 35.85 ± 1.03 | −0.48 ± 2.90 | 30.21 ± 0.12 | 15.33 ± 0.32 |
| 1 μM | 35.36 ± 0.65 | 0.90 ± 1.82 | 35.42 ± 0.43 | 0.74 ± 1.19 | 33.85 ± 0.55 | 5.12 ± 1.53 |
| 0.3 μM | 35.47 ± 0.98 | 0.60 ± 2.74 | 36.35 ± 0.84 | −1.88 ± 2.35 | 34.66 ± 0.20 | 2.87 ± 0.57 |
| 0.1 μM | 35.13 ± 0.22 | 1.54 ± 0.62 | 36.05 ± 0.85 | −1.04 ± 2.39 | 34.68 ± 0.06 | 2.82 ± 0.16 |

The measurement results were fitted by Graphpad Prism 5.0 to calculate $IC_{50}$ values. The fitted results from the software showed that Compound I had $IC_{50}$ of 0.5 mM, Compound II had $IC_{50}$ of 0.4 mM, and quercetin had $IC_{50}$ of 21 μM. It was demonstrated that Compound I and Compound II had a certain degree of inhibitory activity against glucose oxidase and had potential pharmacological activity for the treatment of kidney calculi and nephritis.

Example 13: Comparison of Activity of Inventive Sample by Extraction with Water and Precipitation with Alcohol, LQC-H-2, and 65% Ethanol Ultrasonic Extract in Prior Art (Yuan Chunlin, et al., *Pharmacology and Clinics of Chinese Materia Medica*, 2008, 24(3), 57-58)

The experimental method is the same to Example 5. Animal grouping: control group; LQC-H-2 group (500 mg/kg); LQC-65% ethanol extract group (500 mg/kg); calibration group free of administration of glucose.

Experimental results: the extract of *Glechoma longituba* (Nakai) Kupr., LQC-H-2, at dosage of 500 mg/kg could significantly enhance acute oral glucose tolerance in mice, while 65% ethanol ultrasonic extract of *Glechoma longituba* (Nakai) Kupr. at the same dosage had no significant effect on acute glucose tolerance in mice (FIG. 12), which suggested that the active ingredients in LQC-H-2 extract obtained by the preparation method provided in the present invention were differ from the overall extract obtained by 65% ethanol ultrasonic extraction process, and that LQC-H-2 could effectively improve acute glucose tolerance in mice.

Experimental conclusion: the extract LQC-H-2 obtained according to the *Glechoma longituba* (Nakai) Kupr. extraction process in Preparation Example 1 could significantly enhance acute oral glucose tolerance in mice, while the 65% ethanol ultrasonic extract of *Glechoma longituba* (Nakai) Kupr. (LQC-65% ethanol extract) at the same dosage had no significant effect on acute glucose tolerance in mice.

We claims:

1. A composition comprising an extract of *Glechoma longituba* (Nakai) Kupr. comprising:
   Compound I, luteolin-7-O-[β-glucuronosyl(1→2)β-glucuronic acid]

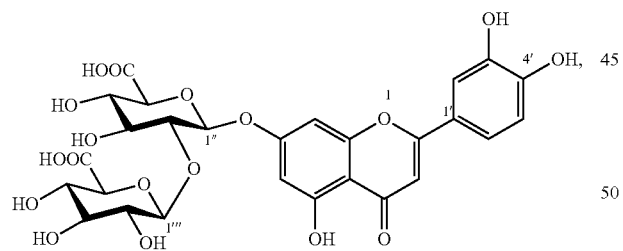

and
   Compound II, apigenin-7-O-[β-glucuronosyl(1→2)β-glucuronic acid]

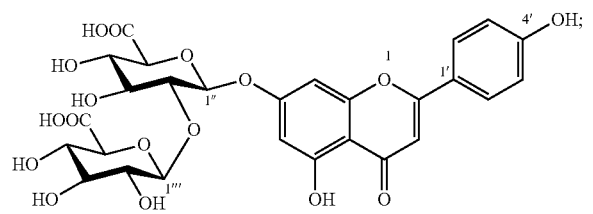

and the weight of both Compound I and Compound II accounts for 1%-75%, of the total weight of the extract, wherein said composition is in form of tablets, hard capsules, soft capsules, enteric capsules, microcapsules, or emulsions.

2. The composition of claim 1, wherein the content of Compound I is more than 0.6%; the content of Compound II is more than 0.6%.

3. The composition of claim 1, wherein contents of caffeic acid and rosmarinic acid are greater than 0% and less than 0.5%.

4. A pharmaceutical composition comprising an effective amount of the composition of claim 1, wherein Compound I and Compound II account for more than 50% of the total weight of active ingredients.

5. The composition of claim 1, wherein the weight of both Compound I and Compound II accounts for 20%-60% of the total weight of the extract.

6. A method of decreasing blood glucose in a patient in need thereof, comprising administering to the patient an effective amount of the composition of claim 1.

7. A method of decreasing blood lipid in a patient in need thereof, comprising administering to the patient an effective amount of the composition of claim 1.

8. A method of losing weight in a patient in need thereof, comprising administering to the patient an effective amount of the composition of claim 1.

9. A method for the treatment of kidney diseases in a patient in need thereof, comprising administering to the patient an effective amount of the composition of claim 1.

10. A method of inhibiting the activity of dipeptidyl peptidase IV in a patient in need thereof, comprising administering to the patient an effective amount of the composition of claim 1.

11. The method of claim 10, wherein the inhibition of the activity of dipeptidyl peptidase IV is to treat diabetes mellitus.

12. A composition comprising an extract of *Glechoma longituba* (Nakai) Kupr. comprising:
   Compound I, luteolin-7-O-[β-glucuronosyl(1→2)β-glucuronic acid]

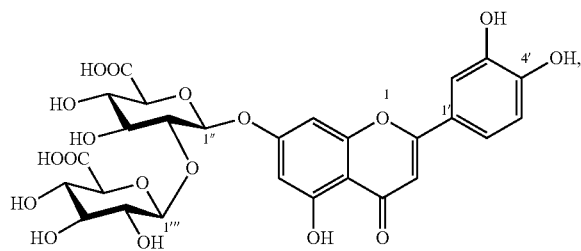

and
   Compound II, apigenin-7-O-[β-glucuronosyl(1→2)β-glucuronic acid]

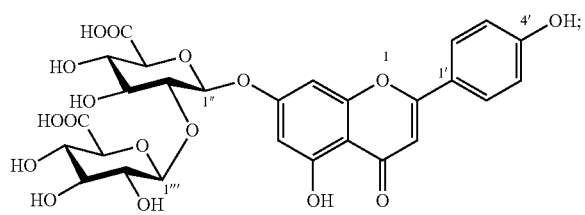

wherein the extract of *Glechoma longituba* (Nakai) Kupr. is obtained by a method comprising:

a) extracting *Glechoma longituba* (Nakai) Kupr. with an aqueous solution one or more times to obtain an aqueous extract liquid of *Glechoma longituba* (Nakai) Kupr., and b) adding to the aqueous extract liquid of *Glechoma longituba* (Nakai) Kupr. a volume of an alcoholic solution to generate a precipitate; and c) separating the precipitate generated in step b), wherein said composition is in form of tablets, hard capsules, soft capsules, enteric capsules, microcapsules, or emulsions.

13. The composition according to claim 12, wherein step a) further comprises the step of concentrating the resulting extract liquid.

14. The composition of claim 12, wherein the aqueous solution in step a) has a water content of more than 40%.

15. The composition of claim 12, wherein the extraction in step a) is extraction by heating reflux or ultrasonic extraction.

16. The composition of claim 12, wherein the aqueous extract liquid of *Glechoma longituba* (Nakai) Kupr. obtained in step a) can also be extracted by an organic solvent, the organic phase is discarded, and the treated aqueous extract liquid of *Glechoma longituba* (Nakai) Kupr. is left for further operation, wherein the organic solvent is ethyl acetate or dichloromethane.

17. The composition of claim 12, wherein the aqueous extract liquid of *Glechoma longituba* (Nakai) Kupr. obtained in step a) can be further refrigerated at 4-6° C., after optional concentration.

18. The composition of claim 12, wherein the alcoholic solution in step b) is a mixed system of ethanol-water.

19. The composition of claim 12, wherein the alcoholic solution in step b) has a volume of 2-4 times of that of the aqueous extract liquid of *Glechoma longituba* (Nakai) Kupr.

20. The composition of claim 12, wherein the precipitate obtained by separation in step c) can be lyophilized.

21. The composition of claim 12, wherein the precipitate obtained by separation in step c) is purified with a macroporous adsorption resin, wherein the purification with a macroporous adsorption resin is performed by:

i) dissolving the precipitate obtained by separation in step c) with an aqueous solvent to prepare an aqueous solution, and removing the residual alcohol;

ii) adding onto the macroporous resin the aqueous solution from which the residual alcohol is removed;

iii) removing components of proteins and polysaccharides with an aqueous eluent; and iv) eluting with an alcoholic eluent and concentrating the resulting eluate to produce a purified extract of *Glechoma longituba* (Nakai) Kupr.

22. The composition of claim 21, wherein the aqueous solution in step i) has a water content of more than 40%.

23. The composition of claim 21, wherein the macroporous resin in step ii) is D-101, D-101-I, DA-201, DM-301, DM-130, AB-8, HPD-100, HPD-300, HPD-400, HPD-600, HPD-826, or fillers similar to these resins.

24. The composition of claim 21, wherein the aqueous eluent in step iii) has a water content more than 90%.

25. The composition of claim 21, wherein the alcoholic eluent in step iv) is a mixed system of ethanol-water.

* * * * *